(12) United States Patent
Foley

(10) Patent No.: US 8,349,011 B2
(45) Date of Patent: Jan. 8, 2013

(54) SYSTEMS AND TECHNIQUES FOR RESTORING AND MAINTAINING INTERVERTEBRAL ANATOMY

(75) Inventor: Kevin T. Foley, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1551 days.

(21) Appl. No.: 11/451,836

(22) Filed: Jun. 13, 2006

(65) Prior Publication Data

US 2006/0229727 A1    Oct. 12, 2006

Related U.S. Application Data

(62) Division of application No. 10/274,856, filed on Oct. 21, 2002, now Pat. No. 7,063,725.

(51) Int. Cl.
*A61F 2/44* (2006.01)

(52) U.S. Cl. .................................................. 623/17.11

(58) Field of Classification Search .................. 606/61, 606/90, 96, 99, 102; 623/17.16; 433/512
See application file for complete search history.

(56) References Cited

U.S. PATENT DOCUMENTS

| | | | |
|---|---|---|---|
| 4,349,921 A | 9/1982 | Kuntz | |
| 4,566,466 A | 1/1986 | Ripple et al. | |
| 4,743,256 A | 5/1988 | Brantigan | |
| 4,834,757 A | 5/1989 | Brantigan | |
| 4,863,476 A | 9/1989 | Shepperd | |
| 4,878,915 A | 11/1989 | Brantigan | |
| 4,950,296 A | 8/1990 | McIntyre | |
| 5,192,327 A | 3/1993 | Brantigan | |
| 5,306,309 A | 4/1994 | Wagner et al. | |
| 5,425,772 A | 6/1995 | Brantigan | |
| 5,443,514 A | 8/1995 | Steffee | |
| 5,445,639 A | 8/1995 | Kuslich et al. | |
| 5,458,638 A | 10/1995 | Kuslich et al. | |
| 5,484,437 A | 1/1996 | Michelson | |
| 5,522,899 A | 6/1996 | Michelson | |
| 5,607,424 A | 3/1997 | Tropiano | |
| 5,609,635 A | 3/1997 | Michelson | |
| 5,645,596 A | 7/1997 | Kim et al. | |
| 5,669,909 A | 9/1997 | Zdeblick et al. | |
| 5,683,463 A | 11/1997 | Godefroy et al. | |
| 5,716,415 A | 2/1998 | Steffee | |
| 5,766,252 A | 6/1998 | Henry et al. | |
| 5,776,199 A | 7/1998 | Michelson | |

(Continued)

FOREIGN PATENT DOCUMENTS

EP     0 493 698 B1     4/1995

(Continued)

OTHER PUBLICATIONS

Tangent—Posterior Discectomy & Grafting Instrumentation Set, Surgical Technique, by Charles L. Branch, Jr., M.D., Wake Forest University, Baptist Medical Center, Winston-Salem, North Carolina; 1999.

*Primary Examiner* — Thomas J Sweet

(57) ABSTRACT

Techniques and systems for distracting a spinal disc space and supporting adjacent vertebrae are provided. Trial instruments are insertable into the disc space to determine a desired disc space height and to select a corresponding implant. Implants can be also be self-distracting and the implant providing the desired disc space height can be implanted in the spinal disc space.

20 Claims, 16 Drawing Sheets

U.S. PATENT DOCUMENTS

| | | | |
|---|---|---|---|
| 5,782,830 | A | 7/1998 | Farris |
| 5,797,909 | A | 8/1998 | Michelson |
| 5,860,973 | A | 1/1999 | Michelson |
| 5,865,845 | A | 2/1999 | Thalgott |
| 5,888,224 | A | 3/1999 | Beckers et al. |
| 5,888,226 | A | 3/1999 | Rogizinski |
| 5,888,227 | A | 3/1999 | Cottle |
| 5,893,890 | A | 4/1999 | Pisharodi |
| 5,895,426 | A | 4/1999 | Scarborough et al. |
| 5,899,939 | A | 5/1999 | Boyce et al. |
| 5,984,922 | A | 11/1999 | McKay |
| 6,025,538 | A | 2/2000 | Yaccarino, III |
| 6,042,582 | A | 3/2000 | Ray |
| 6,045,580 | A | 4/2000 | Scarborough et al. |
| 6,059,829 | A | 5/2000 | Schlapfer et al. |
| 6,080,158 | A | 6/2000 | Lin |
| 6,093,207 | A | 7/2000 | Pisharodi |
| 6,096,038 | A | 8/2000 | Michelson |
| 6,111,164 | A | 8/2000 | Rainey et al. |
| 6,113,639 | A | 9/2000 | Ray et al. |
| 6,123,705 | A | 9/2000 | Michelson |
| 6,123,731 | A | 9/2000 | Boyce et al. |
| 6,143,033 | A | 11/2000 | Paul et al. |
| 6,146,422 | A | 11/2000 | Lawson |
| 6,159,214 | A | 12/2000 | Michelson |
| 6,159,215 | A | 12/2000 | Urbahns et al. |
| 6,174,311 | B1 | 1/2001 | Branch et al. |
| 6,179,873 | B1 | 1/2001 | Zientek |
| 6,200,347 | B1 | 3/2001 | Anderson et al. |
| 6,210,412 | B1 | 4/2001 | Michelson |
| 6,241,771 | B1 | 6/2001 | Gresser et al. |
| 6,245,108 | B1 | 6/2001 | Biscup |
| 6,258,125 | B1 | 7/2001 | Paul et al. |
| 6,264,656 | B1 | 7/2001 | Michelson |
| 6,277,149 | B1 | 8/2001 | Boyle et al. |
| 6,290,724 | B1 | 9/2001 | Marino |
| 6,302,914 | B1 | 10/2001 | Michelson |
| 6,315,795 | B1 | 11/2001 | Scarborough et al. |
| 6,319,257 | B1 | 11/2001 | Carignan et al. |
| 6,325,827 | B1 | 12/2001 | Lin |
| 6,383,221 | B1 | 5/2002 | Scarborough et al. |
| 6,423,095 | B1 | 7/2002 | Van Hoeck et al. |
| 6,425,920 | B1 | 7/2002 | Hamada |
| 6,428,544 | B1 | 8/2002 | Ralph et al. |
| 6,432,140 | B1 | 8/2002 | Lin |
| 6,436,102 | B1 | 8/2002 | Ralph et al. |
| 6,443,987 | B1 | 9/2002 | Bryan |
| 6,447,547 | B1 | 9/2002 | Michelson |
| 6,447,548 | B1 | 9/2002 | Ralph et al. |
| 6,458,158 | B1 | 10/2002 | Anderson et al. |
| 6,458,159 | B1 | 10/2002 | Thalgott |
| 6,468,276 | B1 | 10/2002 | McKay |
| 6,471,725 | B1 | 10/2002 | Ralph et al. |
| 6,478,801 | B1 | 11/2002 | Ralph et al. |
| 6,482,233 | B1 | 11/2002 | Aebi et al. |
| 6,500,206 | B1 | 12/2002 | Bryan |
| 6,530,955 | B2 | 3/2003 | Boyle et al. |
| 6,554,863 | B2 | 4/2003 | Paul et al. |
| 6,562,047 | B2 | 5/2003 | Ralph et al. |
| 6,569,168 | B2 | 5/2003 | Lin |
| 6,607,557 | B1 | 8/2003 | Brosnahan et al. |
| 6,610,065 | B1 | 8/2003 | Branch et al. |
| 6,610,089 | B1 | 8/2003 | Liu et al. |
| 6,626,905 | B1 | 9/2003 | Schmiel et al. |
| 6,719,794 | B2 | 4/2004 | Gerber et al. |
| 6,723,096 | B1 | 4/2004 | Dorchak et al. |
| 6,743,257 | B2 | 6/2004 | Castro |
| 6,746,484 | B1 | 6/2004 | Liu et al. |
| 6,749,636 | B2 | 6/2004 | Michelson |
| 6,890,355 | B2 | 5/2005 | Michelson |
| 2001/0020170 | A1 | 9/2001 | Zucherman et al. |
| 2001/0049560 | A1 | 12/2001 | Paul et al. |
| 2002/0016633 | A1 | 2/2002 | Lin et al. |
| 2002/0058950 | A1 | 5/2002 | Winterbottom et al. |
| 2002/0062153 | A1 | 5/2002 | Paul et al. |
| 2002/0065558 | A1 | 5/2002 | Varga et al. |
| 2002/0087212 | A1 | 7/2002 | James et al. |
| 2002/0161366 | A1 | 10/2002 | Robie et al. |
| 2002/0165550 | A1 | 11/2002 | Frey et al. |
| 2003/0014057 | A1 | 1/2003 | Ralph et al. |
| 2003/0014114 | A1 | 1/2003 | Ralph et al. |
| 2003/0014115 | A1 | 1/2003 | Ralph et al. |
| 2003/0023245 | A1 | 1/2003 | Ralph et al. |
| 2003/0023306 | A1 | 1/2003 | Liu et al. |
| 2003/0023309 | A1 | 1/2003 | Ralph et al. |
| 2003/0083747 | A1 | 5/2003 | Winterbottom et al. |
| 2003/0083748 | A1 | 5/2003 | Lee et al. |
| 2003/0087984 | A1 | 5/2003 | Erbe et al. |
| 2003/0105527 | A1 | 6/2003 | Bresina |
| 2003/0114931 | A1 | 6/2003 | Lee et al. |
| 2003/0125739 | A1 | 7/2003 | Bagga et al. |
| 2003/0135275 | A1 | 7/2003 | Garcia et al. |
| 2003/0135276 | A1 | 7/2003 | Eckman |
| 2003/0139814 | A1 | 7/2003 | Bryan |
| 2003/0149438 | A1 | 8/2003 | Nichols et al. |
| 2003/0199980 | A1 | 10/2003 | Siedler |
| 2004/0102847 | A1 | 5/2004 | Sato et al. |
| 2004/0106996 | A1 | 6/2004 | Liu et al. |
| 2004/0162617 | A1 | 8/2004 | Zucherman et al. |
| 2004/0193159 | A1 | 9/2004 | Zucherman et al. |
| 2006/0217806 | A1* | 9/2006 | Peterman et al. .......... 623/17.11 |

FOREIGN PATENT DOCUMENTS

| | | |
|---|---|---|
| EP | 0 716 840 A2 | 6/1996 |
| EP | 0 834 295 A1 | 4/1998 |
| EP | 1 099 429 A1 | 5/2001 |
| EP | 1 201 207 A1 | 5/2002 |
| FR | 2 727 004 | 11/1994 |
| FR | 2 724 312 | 4/1995 |
| FR | 2 736 538 | 7/1995 |
| FR | 2 742 044 | 12/1995 |
| FR | 2 795 945 | 1/2001 |
| FR | 2 841 124 A1 | 12/2003 |
| WO | WO 01/03615 A1 | 1/2001 |
| WO | WO 01/28465 A2 | 4/2001 |
| WO | WO 01/68005 A2 | 9/2001 |
| WO | WO 02/38086 A1 | 5/2002 |
| WO | WO 03/009786 A1 | 2/2003 |
| WO | WO 03/037228 A2 | 5/2003 |
| WO | WO 2005/072659 A3 | 8/2005 |

* cited by examiner

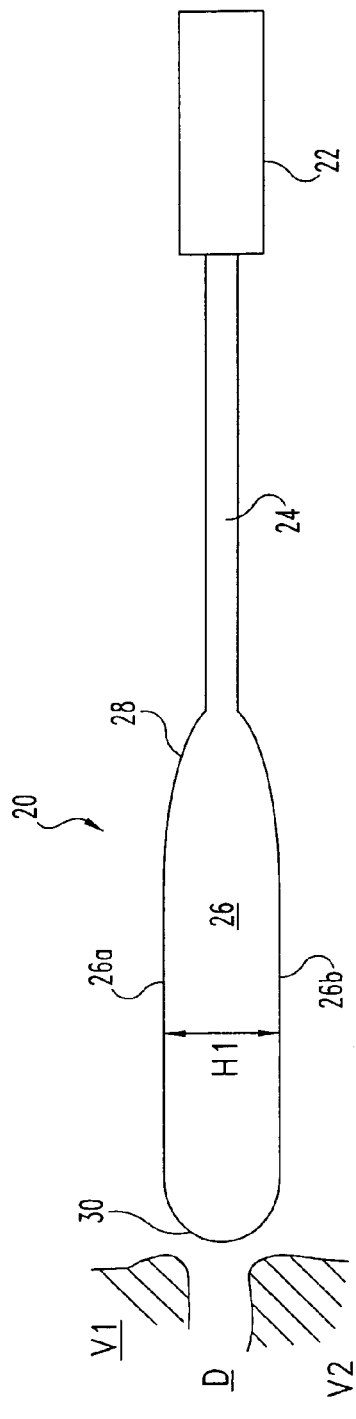
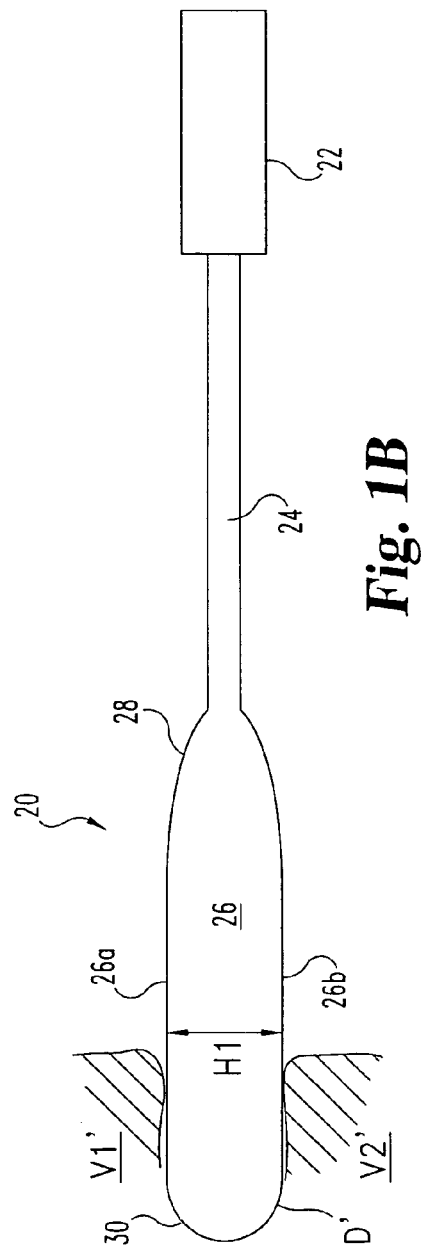

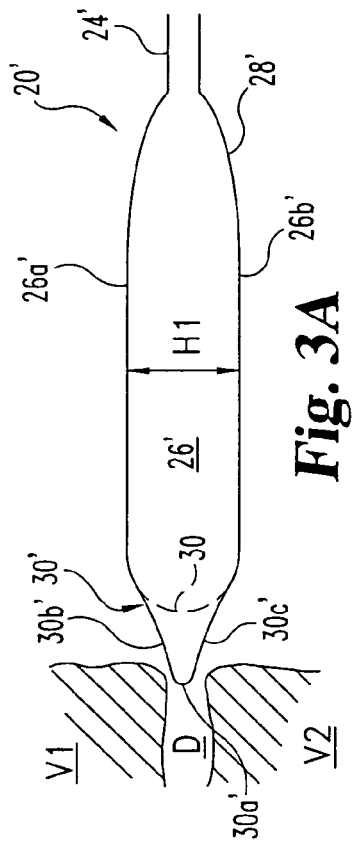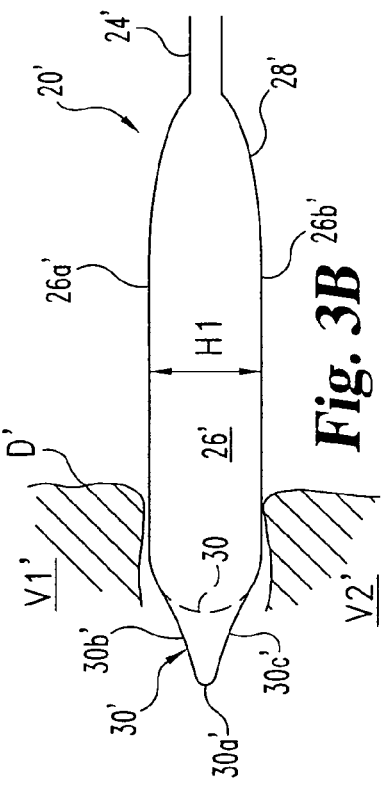
*Fig. 3A*
*Fig. 3B*
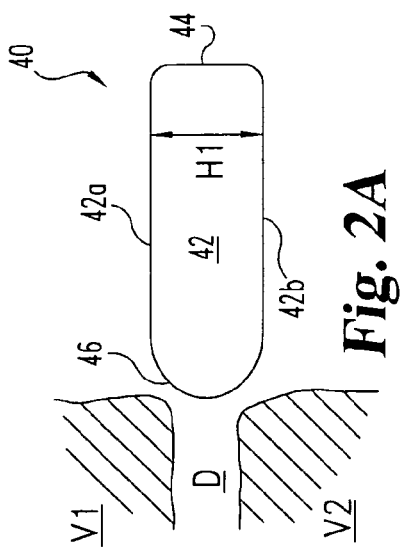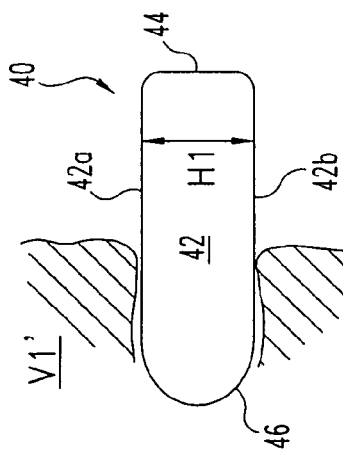
*Fig. 2A*
*Fig. 2B*

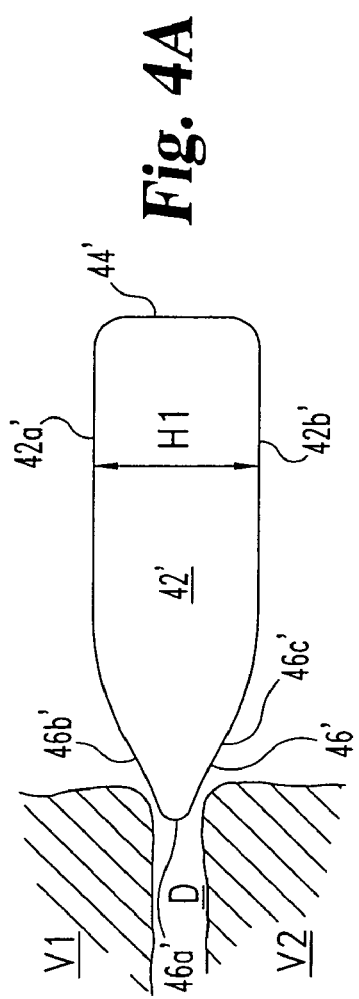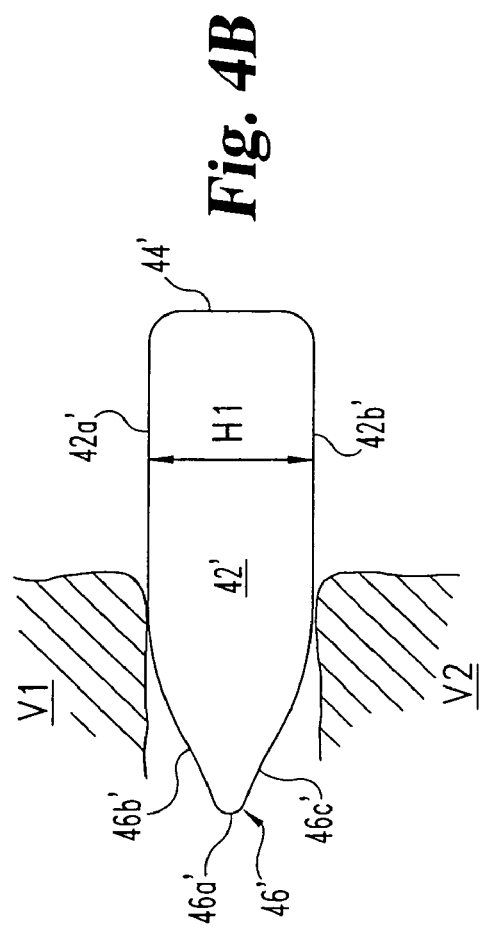

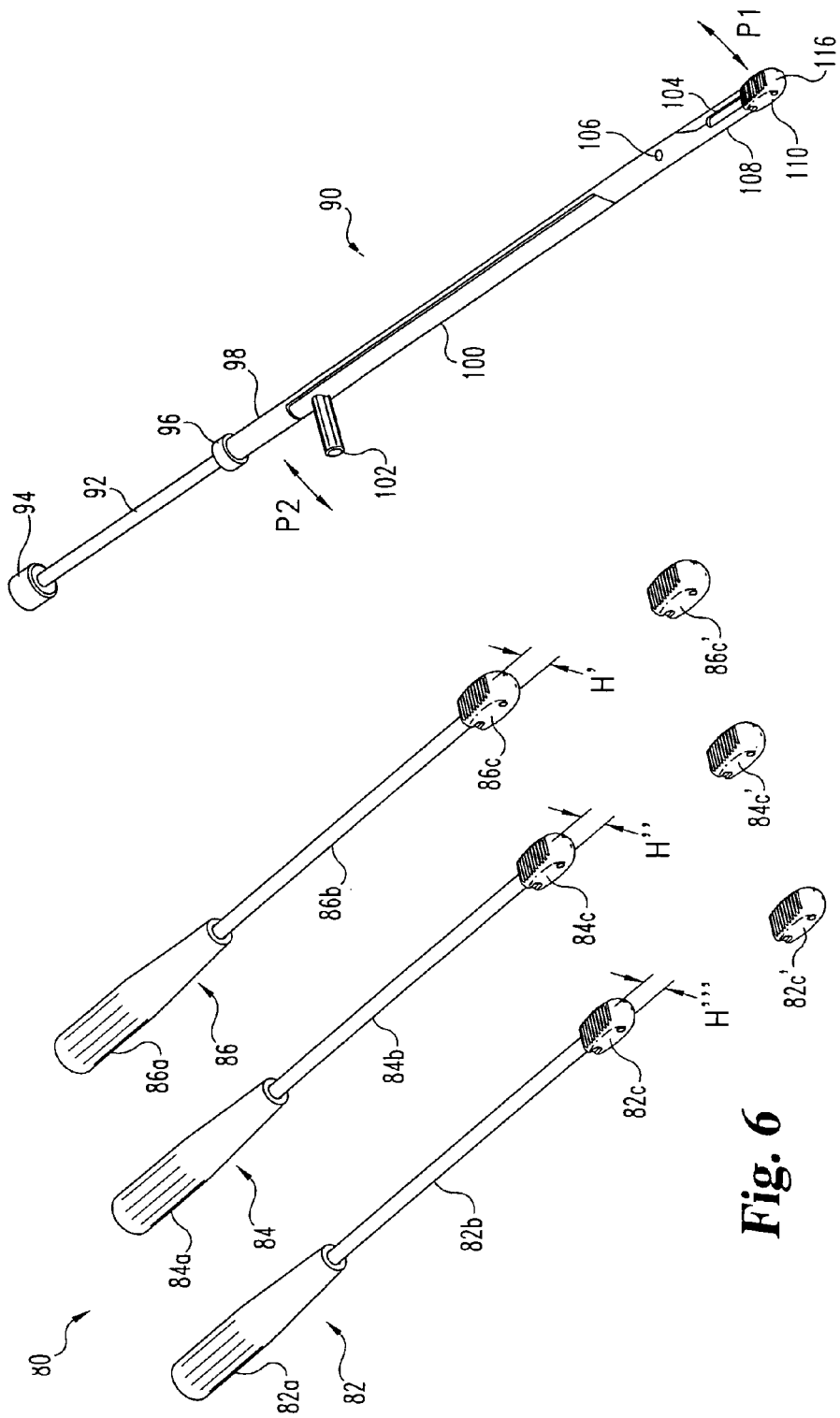

SYSTEMS AND TECHNIQUES FOR RESTORING AND MAINTAINING INTERVERTEBRAL ANATOMY

CROSS-REFERENCE TO RELATED APPLICATION

The present application is a divisional of U.S. patent application Ser. No. 10/274,856 filed on Oct. 21, 2002, and issuing as U.S. Pat. No. 7,063,725, which is incorporated herein by reference.

BACKGROUND

Various surgical instruments and methods have been devised for the implantation of devices into the disc space between adjacent vertebrae of the spinal column. For example, spinal fusion procedures can require sequential distraction to restore the disc space height prior to inserting a pair of fusion devices in the disc space in side-by-side relation. To implant these devices, an initial opening or openings are made in the disc space at the locations through which the devices are to be inserted. A first distractor is inserted in the disc space at one of the device locations. A second larger distractor is inserted in the disc space at the other of the device locations. Sequential distraction in alternate disc space locations is continued until the desired disc space height is achieved. The next to last inserted distractor is then removed. The disc space is prepared for insertion of one fusion device in the location previously occupied by the withdrawn distractor while the other distractor maintains the restored disc space height.

In another technique, a spinal disc space is accessed and distracted for insertion of an implant. Distraction of the disc space is maintained by applying a distraction force to bone screws engaged in the vertebrae on each side of the disc space.

While the above procedure can be effective for some techniques, there are disadvantages. For example, dissection and retraction of tissue, vasculature and nervature is required to accommodate the pair of distractors inserted in the disc space, or to accommodate the external distractors. Alternating sequential distraction can be time-consuming and requires many steps to complete the surgical procedure. Engagement of bone screws to the vertebrae and application of a distraction force to the engaged bone screws also requires additional time and steps in the surgical procedure.

There remains a need for instruments and techniques for restoring and maintaining a spinal disc space anatomy that minimizes dissection and retraction and of tissue, vasculature and nervature. There further remains a need for instruments and techniques for restoring and maintaining a spinal disc space anatomy that minimizes the steps and complexity of the procedure during surgery.

SUMMARY

Implants are provided that can be sequentially inserted and withdrawn from a spinal disc space to restore the disc space to a desired disc space height and to post-operatively maintain the desired spinal disc space height when a selected implant is left in the spinal disc space.

Instruments are provided for determining the desired disc space height and for selecting an implant providing the desired disc space height when inserted in the collapsed disc space.

Implants are provided that can have the same height and leading end portion configuration of at least some trial instruments of a set of trial instruments. Each trial instrument of the set has a trial body providing a restored disc space height and a leading end portion configured to distract the disc space to the restored disc space height.

Implants are provided that have a self-distracting lead end configuration.

Methods for restoring and maintaining a spinal disc space height are provided that include, for example, sequentially inserting and withdrawing a number of implants into a collapsed, non-distracted spinal disc space. The implant providing a desired disc space height is left in the disc space to post-operatively maintain the desired disc space height.

Methods for restoring and maintaining a spinal disc space height are provided that include, for example, sequentially inserting and withdrawing a number of trial bodies into a collapsed spinal disc space. When an inserted trial body is withdrawn, the non-distracted disc space at least partially collapses. Each of the inserted trial bodies has a leading end portion configured to re-distract the disc space after withdrawal of the previous trial body. An inserted trial body is determined to provide a desired disc space height. An implant corresponding in height and leading end portion configuration to the trial body providing the desired disc space height can be inserted into the disc space to restore the collapsed disc space to the desired disc space height and post-operatively maintain the desired disc space height.

Related objects, advantages, aspects, forms, and features of the present invention will be apparent from the following description.

BRIEF DESCRIPTION OF THE DRAWINGS

FIGS. 1A and 1B are elevation views of a self-distracting trial instrument and a pair of adjacent vertebrae before and after insertion of the trial instrument.

FIGS. 2A and 2B are elevation views of a self-distracting implant and a pair of vertebrae before and after insertion of the implant.

FIGS. 3A and 3B are elevation views of a distal portion of another embodiment self-distracting trial instrument and a pair of adjacent vertebrae before and after insertion of the trial instrument.

FIGS. 4A and 4B are elevation views of another embodiment self-distracting implant and a pair of adjacent vertebrae before and after insertion of the implant.

FIG. 6 shows a set of implants and implant insertion instruments.

FIG. 7 is a perspective view of another embodiment implant and implant insertion instrument.

DESCRIPTION OF THE ILLUSTRATED EMBODIMENTS

Figure 5:
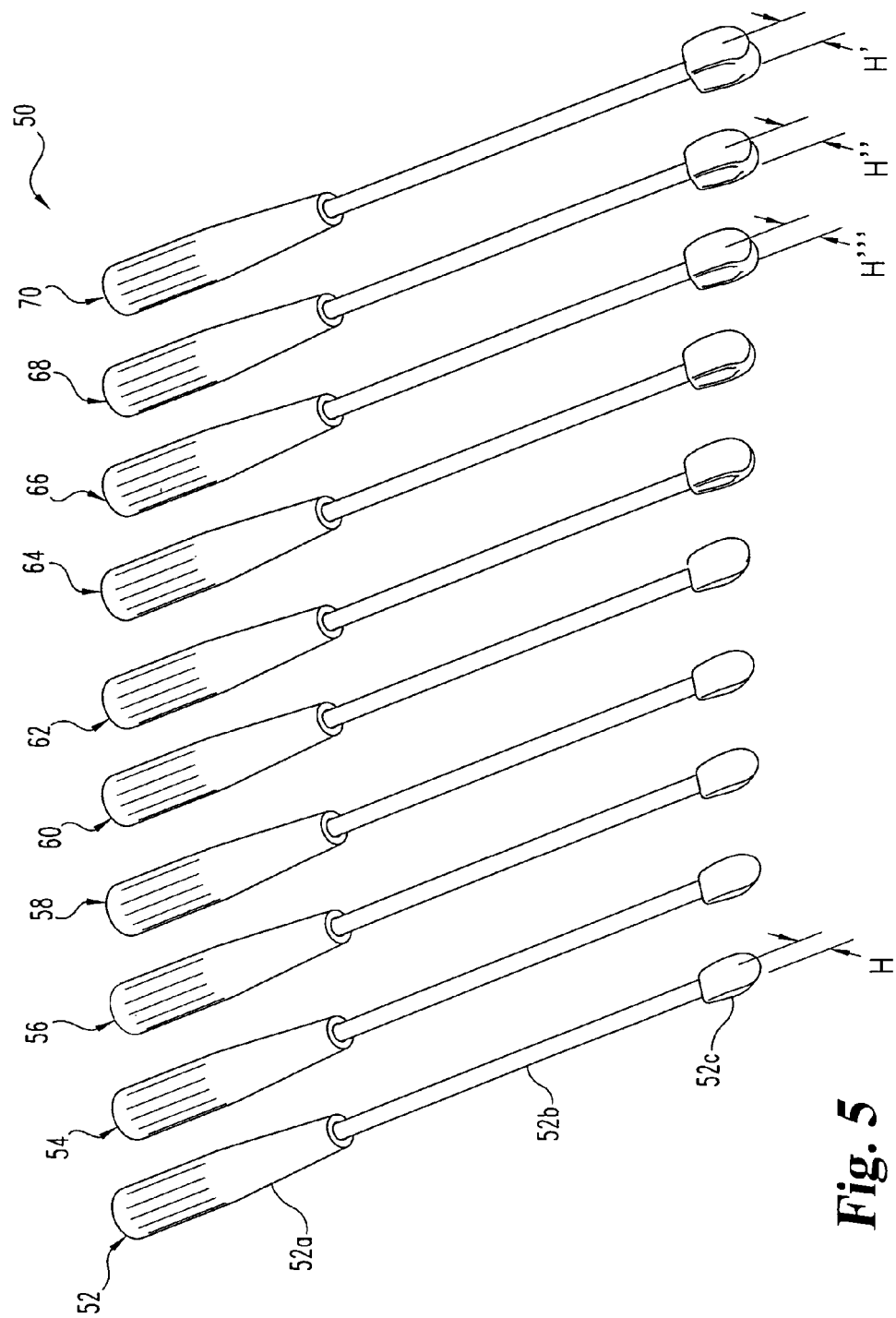
FIG. 5 shows a set of trial instruments.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated device, and any such further applications of the principles of the invention as illustrated therein being contemplated as would normally occur to one skilled in the art to which the invention relates.

Methods, techniques, instrumentation and implants are provided to restore and/or maintain a collapsed spinal disc space at a desired disc space height. The instruments and implants may be used in techniques employing minimally invasive instruments and technology to access the disc space. Access to the collapsed disc space can be uni-portal, bi-portal, or multi-portal. The instruments and implants may also be employed in open surgical procedures in which skin and tissue is dissected and retracted to access the collapsed spinal disc space. The methods, techniques, instruments and implants may also be employed in any surgical approach to the spine, including lateral, antero-lateral, postero-lateral, posterior, and anterior approaches. Also, the surgical methods, techniques, instruments and implants may find application at all vertebral segments of the spine, including the lumbar, thoracic and cervical spinal regions.

Referring now to FIG. 1A, there is shown an implant trial instrument 20 having a proximal handle 22, a shaft 24 extending distally from handle 22, and a trial body 26. Trial body 26 includes a proximal end 28 connected with or formed with a distal end of shaft 24 and a leading insertion end 30. Trial body 26 further includes an upper surface 26a and an opposite lower surface 26b. Trial body has a height H1 between upper surface 26a and lower surface 26b. Proximal end 28 can be tapered or otherwise configured to provide a gradual transition between surfaces 26a, 26b to facilitate withdrawal of trial body 26 from the spinal disc space.

Trial instrument 20 is insertable into a collapsed disc space D between adjacent vertebrae V1 and V2. Leading end portion 30 can be provided with a rounded nose-like shape that allows at least a portion of leading end portion 30 to be inserted into a collapsed, undistracted disc space D. As trial body 26 is advanced into disc space D, the edges of vertebrae V1 and V2 ride upwardly and downwardly, respectively, along the rounded nose portion of leading end portion 30. Once leading end portion 30 is completely inserted, collapsed disc space D is distracted to restore disc space D', as shown in FIG. 1B. Restored disc space D' has a height between the endplates of the adjacent vertebrae V1, V2 which corresponds to height H1 of trial body 26 between upper surface 26a and lower surface 26b.

With trial body 26 inserted in disc space D, the surgeon can determine whether disc space D has been adequately distracted or positioned to a desired disc space height by the tactile feel and visual inspection of trial instrument 20 in the disc space. For example, if trial instrument 20 is easily moved, or does not provide a snug fit, then a trial instrument 20 may be withdrawn and a second trial instrument having a trial body with a greater height H1 is inserted. Alternatively, if the fit of trial body 26 is too tight or won't fit, it can be withdrawn and another trial instrument having a trial body with a smaller height H1 can be inserted in disc space D. The particular trial instrument 20 providing a restored disc space height that corresponds to a desired disc space height is noted by the surgeon for selection of an implant.

In FIG. 2A there is shown an implant 40 having a body 42. Body 42 includes a proximal end 44 and a leading insertion end 46. Body 42 further includes an upper surface 42a and an opposite lower surface 42b. Body 42 has a height H1 between surfaces 42a, 42b. Leading insertion end 46 is the same size and shape as leading end portion 30 of trial body 26. Height H1 between surfaces 42a, 42b of implant body 42 is also the same of height H1 between surfaces 26a, 26b of trial body 26.

In use, implant 40 can be selected from a set of implants corresponding in size and shape with a set of trial instrument bodies 26. The selected implant corresponds in size and shape with the trial body 26 providing the desired fit and desired disc space height for collapsed disc space D. Once implant 40 is selected, trial body 26 is withdrawn from restored disc space D', and restored disc space D' at least partially collapses. Implant 40 has a leading end portion 46 that is the same size and shape as that of trial body 26, and implant 40 will be insertable into the collapsed disc space D since trial body 26 was insertable in collapsed disc space D. Implant 40 restores and post-operatively maintains the collapsed disc space D at a desired disc space height H1 between vertebrae V1 and V2, as shown in FIG. 2B.

Referring to FIG. 3A, an alternate embodiment trial instrument 20' is shown. Trial instrument 20' can include a proximal handle (not shown), a shaft 24 extending distally from the handle, and a trial body 26'. Trial body 26' includes a proximal end 28' connected with or formed with a distal end of shaft 24' and a leading insertion end 30'. Trial body 26' further includes an upper surface 26a' and an opposite lower surface 26b'. Trial body has a height H1 between upper surface 26a' and lower surface 26b'. Proximal end 28' can be tapered or otherwise configured to provide a gradual transition between surfaces 26a', 26b' to facilitate withdrawal of trial body 26' from the spinal disc space.

Trial instrument 20' is insertable into a collapsed disc space D between adjacent vertebrae V1 and V2. Leading end portion 30' can be provided with an aggressively tapered nose portion as compared to leading end portion 30, which is overlaid on leading end portion 30' in FIG. 3A for comparison. Leading end portion 30' can have a pointed or blunt end nose portion 30a'. Nose portion 30a' can be relatively small in height for insertion into a severely collapsed disc space D. For example, the height of nose portion 30a' can be in the range from 3 millimeters or less to about 5 or 6 millimeters. Leading end portion 30' further includes an upper transition surface 30b' and a lower transition surface 30c'. Transition surfaces 30b', 30c' extend from nose portion 30a' to respective ones of the upper surface 26a' and lower surface 26b'. Transition surfaces 30b', 30c' provide a smooth and gradual transition for separation of collapsed vertebrae V1 and V2 as trial body 26' is advanced into collapsed disc space D. As shown in FIG. 3B, once leading end portion 30' is completely inserted, collapsed disc space D is distracted or restored by body 26'. Vertebrae V1' and V2' can be separated by height H1 to provide restored disc space D' having a height between the endplates of the adjacent vertebrae which corresponds to height H1 of trial body 26' between upper surface 26a' and lower surface 26b'.

In FIG. 4A there is shown an implant 40' having a body 42'. Body 42' includes a proximal end 44' and a leading insertion end 46'. Body 42' further includes an upper surface 42a' and an opposite lower surface 42b'. Body 42' has a height H1 between surfaces 42a', 42b'. Leading insertion end 46' is the same size and shape as leading end portion 30' of trial body 26'. Height H1 between surfaces 42a', 42b' of implant body 42' has height H1 between surfaces 26a', 26b' of trial body 26'.

Leading end portion 46' can be provided with an aggressively tapered nose portion such as that provided with leading end portion 30' of trial instrument 20'. Leading end portion 46' can have a pointed or blunt nose portion 46a'. Nose portion 46a' can be relatively small in height for insertion into a severely collapsed disc space D. For example, the height of nose portion 46a' can range from 3 millimeters or less to about 5 to 6 millimeters. Leading end portion 46' further includes an upper transition surface 46b' and a lower transition surface 46c'. Transition surfaces 46b', 46c' extend from nose portion 46a' to respective ones of the upper surface 42a' and lower surface 42b'. Transition surfaces 46b', 46c' provide a smooth and gradual transition for separation of collapsed vertebrae V1 and V2 as implant body 42' is advanced into collapsed disc space D. Leading end portion 46' is completely inserted to restore collapsed disc space D. As shown in FIG. 4B, the distracted or restored disc space D' between vertebrae V1' and V2' has a height between the endplates of the adjacent vertebrae V1', V2' which corresponds to the height H1 of implant body 42' between upper surface 42a' and lower surface 42b'.

In use, implant 40' can be selected from a set of implants having similar configurations but different heights H1. Implant 40' can be selected to correspond in height with the trial body 26' providing the desired fit and desired disc space height for collapsed disc space D. Once implant 40' is selected, the last inserted trial body 26' is withdrawn from restored disc space D', and restored disc space D' collapses. However, since leading end portion 46' of implant 40' is the same as that of leading end portion 30' of trial body 26', and the last inserted trial body 26' was insertable in the collapsed disc space D, the selected implant 40' will also be insertable in the collapsed disc space D. Implant 40' thus provides a restored disc space D' corresponding to the desired disc space height indicated by trial body 26', and the selected and inserted implant 40' post-operatively maintains the restored disc space D' at a desired disc space height H1.

In the embodiments of FIGS. 1A-4B, it is contemplated that implants 40, 40' could be releasably attachable to the distal end of shaft 24 for insertion into collapsed disc space D. It is further contemplated that, rather than providing separate trial instruments, a series of implants 40, 40' could be provided of increasing height H1. The surgeon could insert and, if necessary, withdraw various ones of the implants 40, 40' to determine which of the various height implants provide a desired disc space height. The implant providing the desired disc space height can be left in the disc space to post-operatively maintain the desired disc space height. The number of steps in the surgical procedure and time required for surgery can be further reduced by providing such self-distracting implants that do not require pre-distraction of the collapsed disc space for insertion. However, providing trial instruments can be advantageous for implants made from some types of bone material or other material that may not withstand impaction into a collapsed disc space since the trial instruments provide an indication that the implant will fit before it is impacted into the disc space, reducing the chance of damaging the implant during withdrawal or during insertion.

It is further contemplated that implants 40' can be provided in a set of implants having increasing heights H1. The height at leading end portion 46' can be the same for each implant 40' of the set so that any of the implants of the set could be selected for insertion into the collapsed disc space when it is initially accessed. Sequential distraction with the implants 40' may not be needed or can be minimized if one of the first selected implants provides the desired disc space height and fit. For example, each of the various height implants 40' of the set can include transition surfaces 46b', 46c' that taper from the same height nose portion 46a' provided on each implant to the differing heights H1 between upper and lower surfaces 42a', 42b' provided on each implant.

In FIG. 5 there is shown a trial instrument set 50 having a number of trial instruments 52, 54, 56, 58, 60, 62, 64, 66, 68 and 70. Trial instrument 52 includes a handle 52a, a shaft 52b extending distally from handle 52a, and a trial body 52c. Each of the other trial instruments also includes a handle, a shaft and a trial body. It is contemplated that each trial body of the trial instruments provides a different height between an upper and a lower contact surface thereof for restoring a collapsed disc space. For example, trial instrument 52 can be provided with a trial body having the smallest height H of the instrument set 50, and trial instrument 70 can be provided with a trial body having the largest height H' of the instrument set 50. The remaining trial instruments can provide a number of different height trial instruments ranging in height between H and H'. In one particular embodiment of instrument set 50, the height of the trial instruments in the set increase in one millimeter increments. In another particular embodiment, the heights range from 6 millimeters to 15 millimeters in one millimeter increments. Other increments and other ranges of heights are also contemplated.

In FIG. 6 there is shown a set 80 of implant insertion instruments 82, 84, 86. Implant insertion instrument 82 includes a handle 82a, a shaft 82b, and an implant 82c releasably coupled to the distal end of shaft 82b. Implant 82c can have a height H''' between its upper and lower vertebral contacting surfaces. Implant insertion instrument 84 includes a handle 84a, a shaft 84b, and an implant 84c releasably coupled to the distal end of shaft 84b. Implant 84c can have a height H'' between its upper and lower vertebral contacting surfaces. Implant insertion instrument 86 includes a handle 86a, a shaft 86b, and an implant 86c releasably coupled to the distal end of shaft 86b. Implant 86c can have a height H' between its upper and lower vertebral contacting surfaces. As further shown in FIG. 6, each of the implants 82c, 84c, 86c is releasable from its insertion instrument so that any one of implants 82c, 84c, 86c can be selected for insertion and post-operative implantation in the disc space.

It is contemplated that implant insertion instrument set 80 can be provided with trial instrument set 50. Each of the implants can be preloaded on an instrument shaft to save time during surgery. However, each of the implants could also be provided separated with a single instrument shaft and then, when the desired implant height is determined, the appropriate implant coupled to the instrument shaft. Heights H''', H'', and H' of implants 82c, 84c, 86c correspond to the heights H''', H'', H' of the trial bodies of trial instruments 66, 68, and 70, respectively. Accordingly, the surgeon determines which of the trial bodies of trial instruments 66, 68 or 70 has a height providing the desired fit in the disc space by alternately inserting selected ones of the trial bodies in the disc space. The trial body providing the desired disc space height is removed and the implant insertion instrument providing an implant with the same height is selected, and the implant is inserted into the disc space to restore and maintain the desired disc space height.

It is contemplated that more than three implant insertion instruments 82, 84, 86 could be provided with implant insertion instrument set 80. For example, a set of implant insertion instruments could be provided with implants each having a height corresponding to the height of one of the trial bodies of trial instrument set 50. It is further contemplated that, rather than providing any trial instrument set 50, an implant insertion instrument set 80 can be provided with a number of implants providing the desired range of heights. The implants of the implant insertion instrument set are sequentially inserted and, if necessary, withdrawn from the collapsed disc space. The implant providing the desired fit and desired disc space height is left in the disc space to post-operatively maintain the disc space height.

In FIG. 7 there is shown an implant 110 coupled to the distal end of an insertion instrument 90. Insertion instrument 90 includes a proximal shaft 92 and a proximal end cap 94. An intermediate hub 96 is located at the distal end of proximal shaft 92. A slap hammer or other instrument for assisting in impacting implant 110 into a disc space can be secured about proximal shaft 92 and impacted against end cap 94 and/or hub 96.

Extending distally from hub 96 is an actuator assembly including a first member 98 and a second member 100. First member 98 includes a coupling portion 108 at its distal end, and second member 100 includes a coupling portion 104 at its distal end. First and second members 98, 100 are pivotally coupled at pin 106 so that at least one of the coupling portions 104, 108 is movable relative to the other coupling portion about pin 106. In the illustrated embodiment, coupling portion 104 is movable about pin 106 in the directions of arrow P1 by moving handle 102 in the directions of arrows P2 to engage and release implant 110 between coupling members 104, 108.

In one embodiment, implant 110 is comprised of two or more pieces of material that can be temporarily or permanently joined together, and can be held together by insertion instrument 90 during insertion into the disc space. Implant 110 includes a self-distracting leading end portion 116 to facilitate insertion in a collapsed disc space. In another embodiment, implant 110 is comprised of a single piece of material. The material comprising implant 110 can be solid, porous, multiply drilled, perforated, open and/or spongy, for example.

Figure 10B:
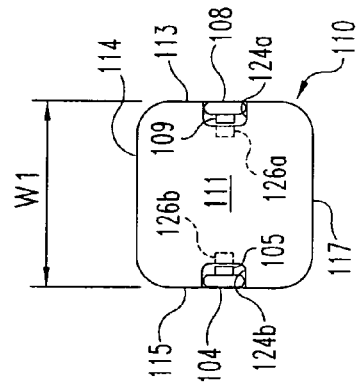
FIG. 10B is an elevation view of the proximal end of the implant of FIG. 7 uncoupled from the insertion instrument.
Figure 10A:
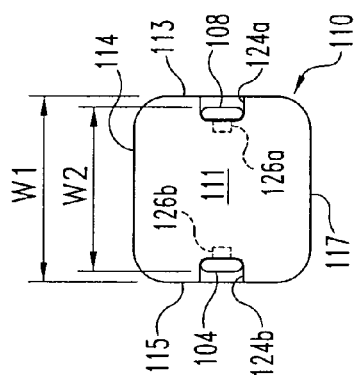
FIG. 10A is an elevation view of a proximal end of the implant of FIG. 7 coupled to the insertion instrument.
Figure 8:
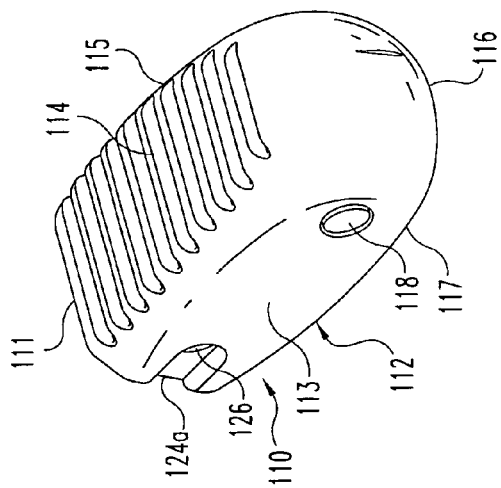
FIG. 8 is a perspective view of an embodiment of the implant of FIG. 7.

Further details regarding one embodiment of implant 110 are shown in FIG. 8. Implant 110 includes a body 112 with an upper surface 114 and an opposite lower surface 117. The upper and lower surfaces 114, 117 can be provided with grooves, recesses, ridges, serrations, knurlings, spikes, roughened surfaces, or smooth surfaces for engaging the endplates of the adjacent vertebrae. Body 112 includes a leading end portion 116 that is rounded or tapered configured so that body 112 distracts the adjacent vertebrae as it is inserted in a collapsed disc space. Body 112 also includes a proximal end wall 111, and sidewalls 113, 115 extending between proximal end wall 111 and leading end portion 116. As shown in FIGS. 10A and 10B, a first notch 124a in lateral wall 113 and a second notch 124b in lateral wall 115 each extend distally from and open at proximal end wall 111. First notch 124a can be provided with an indent 126a therein, and second notch 124 can be provided with an indent 126b therein.

Figure 9:
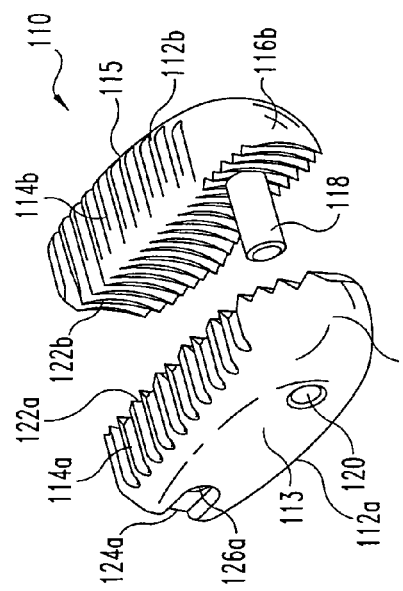
FIG. 9 is an exploded perspective view of the implant of FIG. 8.

In FIG. 9, implant 112 is shown in an exploded view. Body 112 can be provided in a first lateral section 112a and a second lateral section 112b. Lateral sections 112a, 112b each include a corresponding portion of the upper surface 114a, 114b, the lower surface, and leading end portion 116a, 116b. One of the lateral sections, such as lateral section 112a, can be provided with a bore 120, and the other of the lateral sections, such as lateral section 112b can be provided with a pin 118. Pin 118 is insertable into bore 120 to secure lateral sections 112a, 112b to one another. Lateral section 112a includes a medial surface 122a and lateral section 112b includes a medial surface 122b. Medial surfaces 122a, 122b are positioned adjacent one another when lateral sections 112a, 122b are assembled. Medial surfaces 122a, 122b can each be provided with peaks and valleys that interdigitate with peaks and valleys of the other medial surface to assist in holding lateral sections 112a, 112b together and prevent relative movement there between. In the illustrated embodiment, the peaks and valleys extend in the direction between upper surface 114 and lower surface 117. Other orientations for the peaks and valleys are also contemplated, such as extending between leading end portion 116 and proximal end 111, or extending diagonally.

In the embodiment of implant 110 discussed above, it is contemplated that implant 110 can be made of cortical bone cut so that the longitudinal axes of lateral sections 112a, 112b between leading end portions 116a, 116b and proximal end 111 are parallel to the longitudinal axis of the host bone from which the sections are cut. By cutting through the host bone longitudinally to obtain the implant sections, leading end portion 116 of implant 110 is provided with maximum strength and durability to withstand impaction of implant 110 into the disc space. Other embodiments of implant 110 contemplate that implant 110 is provided as an integral unit, and can be made from a single piece of bone material, or made from non-bone material.

As shown in FIGS. 10A and 10B, the coupling portions 104, 108 are positionable in notches 124a, 124b to engage implant 110 to insertion instrument 90. Coupling portion 104 can include a protrusion 105 positionable in detent 126b, and coupling portion 108 can include a protrusion 109 positionable in detent 126a. In FIG. 10A, coupling portions 104, 108 define a width W2 between the lateral outside edges thereof that is less than a width W1 between lateral walls 113, 115 of implant 110. Thus, coupling portions 104, 108 and insertion instrument 90 do not protrude laterally from implant 110 during insertion. As shown in FIG. 10B, coupling portions 104, 108 are moved away from one another to disengage implant 110 and to remove protrusions 105, 109 from detents 126b, 126a, respectively so that insertion instrument 90 can be longitudinally withdrawn from implant 110. The width between the lateral outside edges of coupling members 104, 108 can be limited in the uncoupled position to be the same as or less than width W1 of implant 110. In this manner, insertion instrument 90 can be uncoupled from implant 110 while maintaining a low profile that does not protrude or project laterally beyond lateral walls 113, 115. As a result, the pathway through which implant 110 is positioned to the collapsed disc space need only be large enough to accommodate implant 110.

Figure 11A:
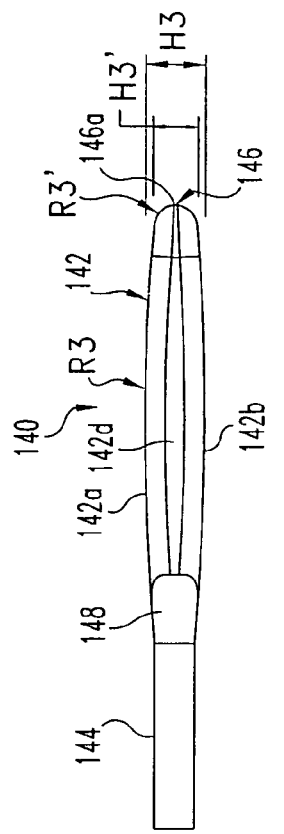
FIGS. 11A and 11B are a plan view and side view, respectively, of a distal portion of another embodiment trial instrument.
Figure 11B:
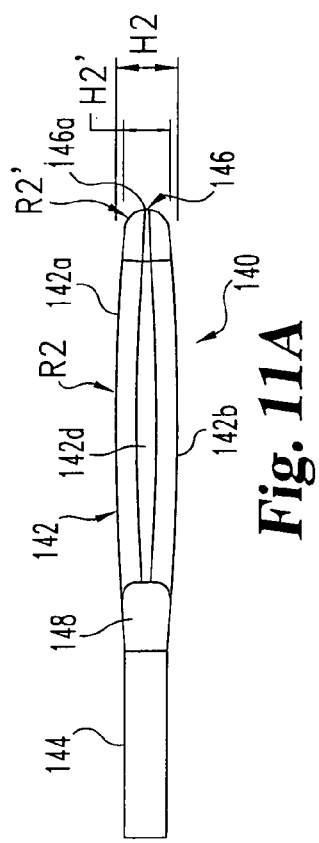

Referring now to FIGS. 11A-11B, there is shown an embodiment of a distal portion 140 of a trial instrument attachable to an insertion instrument. Other embodiment distal portions 140 for trial instruments are shown FIGS. 12A-20B that are similar to the distal portion of FIG. 11A but with differing geometrical properties for determining a desired disc space height. However, as discussed further below, the distal portions of FIGS. 12A-20B have geometrical properties which differ from distal portion 140, providing a set of distal portions 140 which can be sequentially inserted and withdrawn from a collapsed spinal disc space to determine an appropriate implant for insertion therein. In addition, it is contemplated that implants could be provided having the same size and shape of each of the trial bodies of distal portions 140 shown in FIGS. 11A-20B.

Distal portion 140 includes a trial body 142 and a shaft coupling portion 144 extending proximally from trial body 142. Shaft coupling portion 144 can be coupled to an insertion instrument. Other embodiments contemplate that trial body 142 can be integral with the insertion instrument. Contemplated coupling arrangements between trial body 142 and the insertion instrument include clamping connections, frictional connections, set screw connections, threaded connections, bayonet connections, and ball-detent connections, for example. Trial body 142 includes an upper surface 142a and a lower surface 142b for contacting the endplate of the adjacent vertebra. Trial body 142 also includes lateral surfaces 142c and 142d. Rounded or tapered lateral transition surfaces extend between upper and lower surfaces 142a, 142b and the respective lateral surfaces 142c, 142d. Trial body 142 further includes a leading end portion 146 and a proximal end 148. Proximal end 148 can be tapered to facilitate withdrawal of trial body 142 from the disc space. Leading end portion 146 includes a nose portion 146a and rounded portions transitioning to the upper and lower surfaces 142a, 142b.

Distal portion 140 includes an overall length L1, and trial body 142 includes a length L2. Upper and lower surfaces 142a, 142b can be curved along a radius R2 to generally mate with the vertebral endplate geometry. The upper and lower transition surfaces of leading end portion 146 can be curved along radius R2'. Trial body 142 includes an overall maximum height H2 between upper and lower surfaces 142a, 142b. Upper and lower surfaces 142a, 142b can be curved to provide a height H2' at leading end 146. Height H2' is less than height H2 to facilitate insertion of leading end portion 146 into the spinal disc space. Trial body 142 can be provided with an overall width W3 between lateral surfaces 142c and 142d.

Figure 12A:
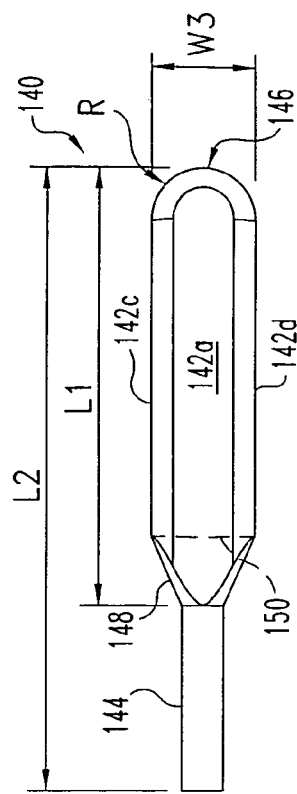
FIGS. 12A and 12B are a plan view and side view, respectively, of a distal portion of another embodiment trial instrument.
Figure 12B:
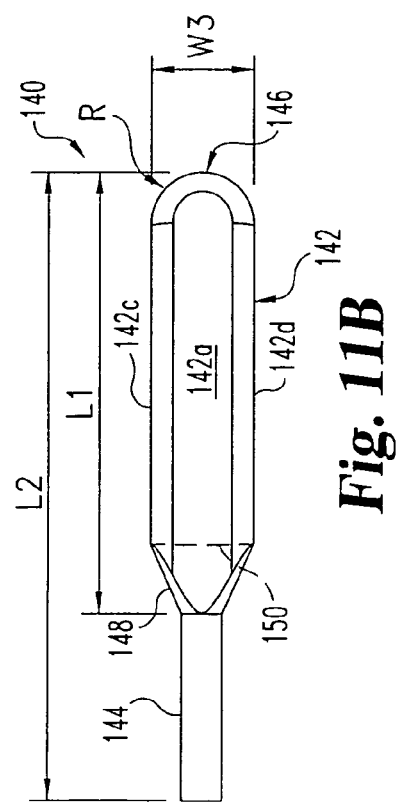

In FIGS. 12A and 12B, distal portion 140 is provided with a body 142 having upper and lower surfaces 142a, 142b curved along radius R3. The upper and lower transition surfaces of leading end portion 146 are curved along radius R3'. Trial body 142 has an overall maximum height H3 between upper and lower surfaces 142a, 142b. Upper and lower surfaces 142a, 142b are curved to provide a height H3' at leading end portion 146. Height H3' is less than height H3 to facilitate insertion of leading end portion 146 into the spinal disc space.

Figure 13A:
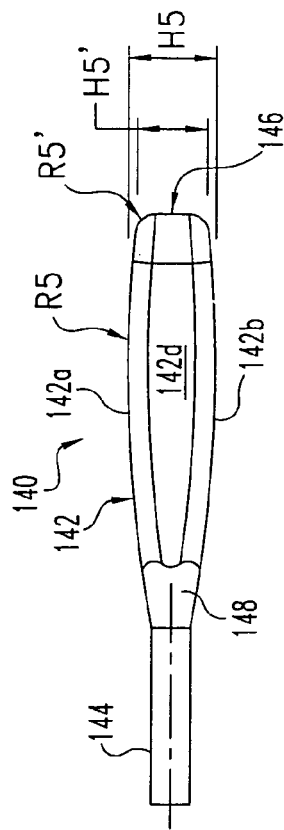
FIGS. 13A and 13B are a plan view and side view, respectively, of a distal portion of another embodiment trial instrument.
Figure 13B:
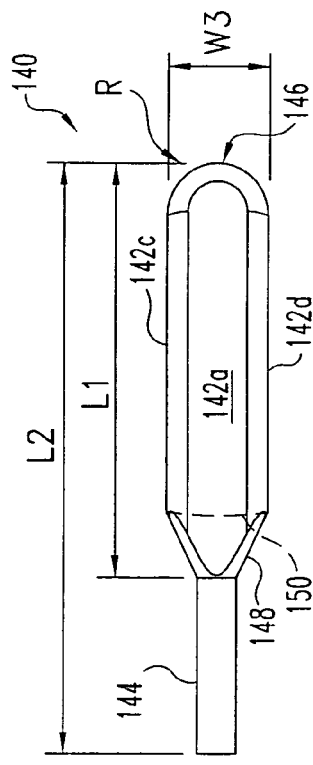

In FIGS. 13A and 13B, distal portion 140 is provided with a body 142 having upper and lower surfaces 142a, 142b curved along radius R4. The upper and lower transition surfaces of leading end portion 146 are curved along radius R4'. Trial body 142 has an overall maximum height H4 between upper and lower surfaces 142a, 142b. Upper and lower surfaces 142a, 142b are curved to provide a height H4' at leading end portion 146. Height H4' is less than height H4 to facilitate insertion of leading end portion 146 into the spinal disc space.

Figure 14A:
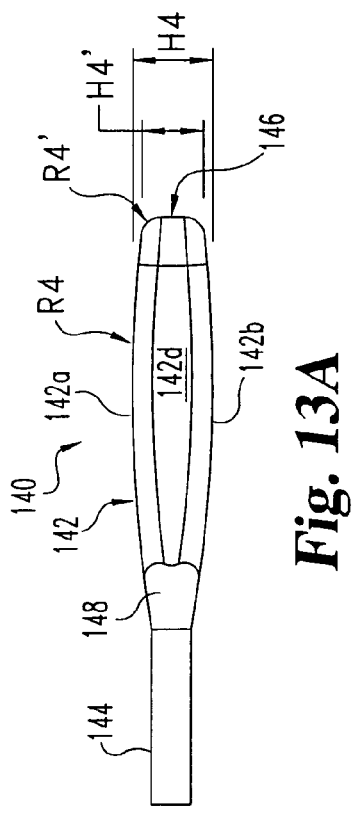
FIGS. 14A and 14B are a plan view and side view, respectively, of a distal portion of another embodiment trial instrument.
Figure 14B:
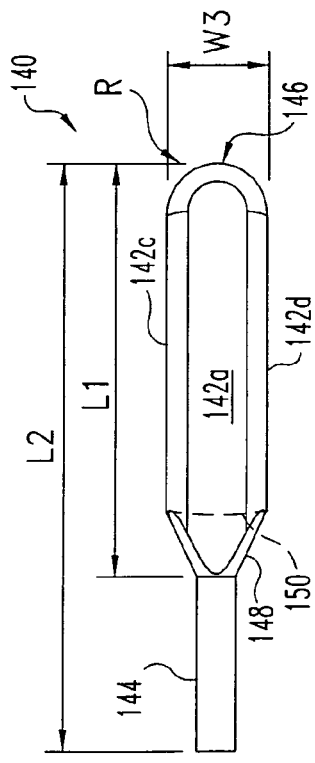

In FIGS. 14A and 14B, distal portion 140 is provided with a body 142 having upper and lower surfaces 142a, 142b curved along radius R5. The upper and lower transition surfaces of leading end portion 146 are curved along radius R5'. Trial body 142 has an overall maximum height H5 between upper and lower surfaces 142a, 142b. Upper and lower surfaces 142a, 142b are curved to provide a height H5' at leading end portion 146. Height H5' is less than height H5 to facilitate insertion of leading end portion 146 into the spinal disc space.

Figure 15A:
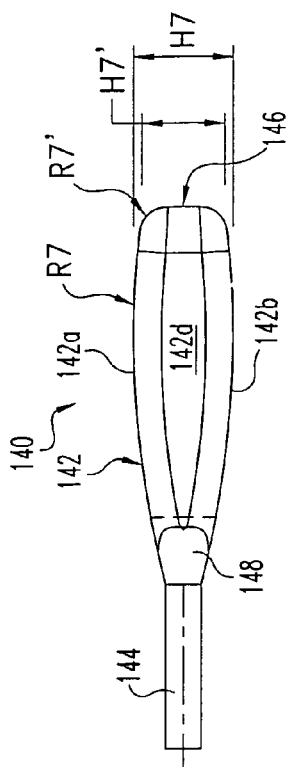
FIGS. 15A and 15B are a plan view and side view, respectively, of a distal portion of another embodiment trial instrument.
Figure 15B:
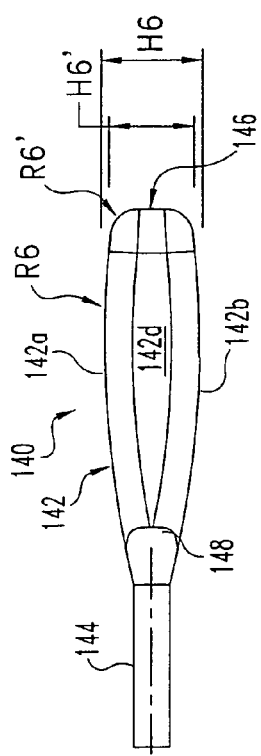

In FIGS. 15A and 15B, distal portion 140 is provided with a body 142 having upper and lower surfaces 142a, 142b curved along radius R6. The upper and lower transition surfaces of leading end portion 146 are curved along radius R6'. Trial body 142 has an overall maximum height H6 between upper and lower surfaces 142a, 142b. Upper and lower surfaces 142a, 142b are curved to provide a height H6' at leading end portion 146. Height H6' is less than height H6 to facilitate insertion of leading end portion 146 into the spinal disc space.

Figure 16A:
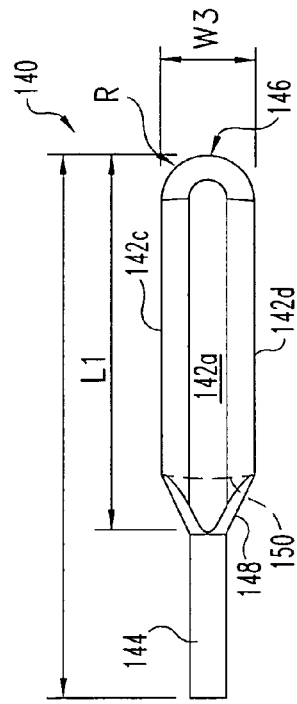
FIGS. 16A and 16B are a plan view and side view, respectively, of a distal portion of another embodiment trial instrument.
Figure 16B:
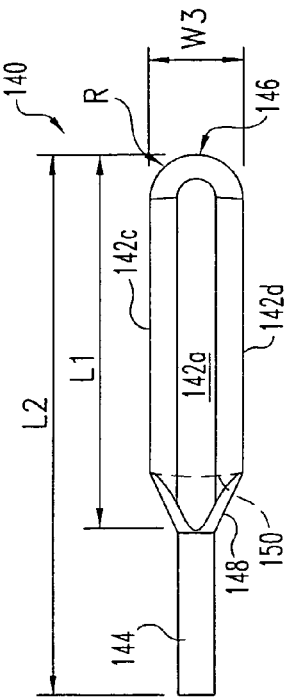

In FIGS. 16A and 16B, distal portion 140 is provided with a body 142 having upper and lower surfaces 142a, 142b curved along radius R7. The upper and lower transition surfaces of leading end portion 146 are curved along radius R7'. Trial body 142 has an overall maximum height H7 between upper and lower surfaces 142a, 142b. Upper and lower surfaces 142a, 142b are curved to provide a height H7' at leading end portion 146. Height H7' is less than height H7 to facilitate insertion of leading end portion 146 into the spinal disc space.

Figure 17A:
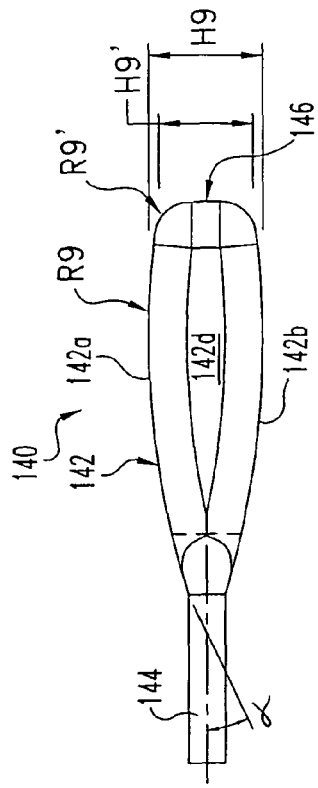
FIGS. 17A and 17B are a plan view and side view, respectively, of a distal portion of another embodiment trial instrument.
Figure 17B:
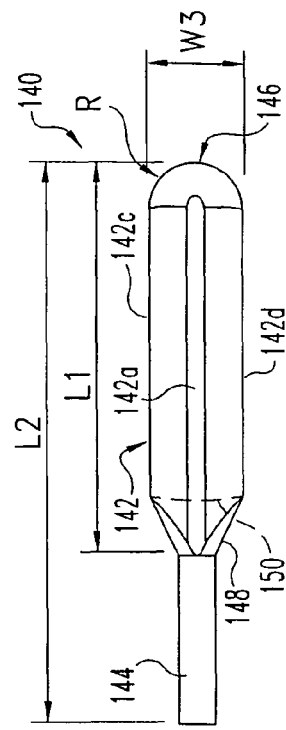

In FIGS. 17A and 17B, distal portion 140 is provided with a body 142 having upper and lower surfaces 142a, 142b curved along radius R8. The upper and lower transition surfaces of leading end portion 146 are curved along radius R8'. Trial body 142 has an overall maximum height H8 between upper and lower surfaces 142a, 142b. Upper and lower surfaces 142a, 142b are curved to provide a height H8' at leading end portion 146. Height H8' is less than height H8 to facilitate insertion of leading end portion 146 into the spinal disc space. Upper and lower surfaces 142a, 142b further taper along proximal end 148 to form angle α with the central axis of the insertion instrument. Angle α provides a smooth transition between coupling portion 144 and body 142 to prevent body 142 from hanging up or catching on the vertebral endplates as it is withdrawn.

Figure 18A:
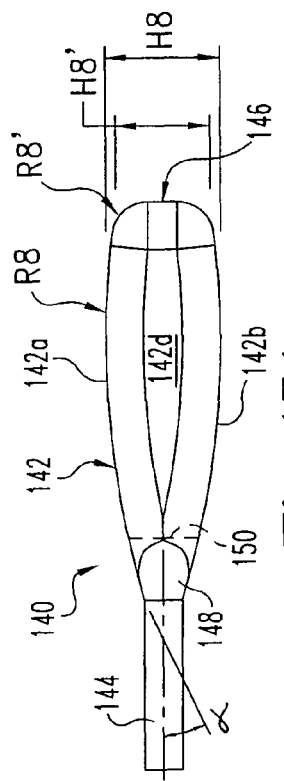
FIGS. 18A and 18B are a plan view and side view, respectively, of a distal portion of another embodiment trial instrument.
Figure 18B:
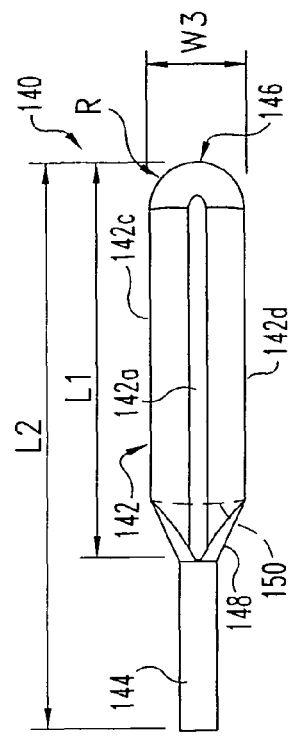

In FIGS. 18A and 18B, distal portion 140 is provided with a body 142 having upper and lower surfaces 142a, 142b curved along radius R9. The upper and lower transition surfaces of leading end portion 146 are curved along radius R9'. Trial body 142 has an overall maximum height H9 between upper and lower surfaces 142a, 142b. Upper and lower surfaces 142a, 142b are curved to provide a height H9' at leading end portion 146. Height H9' is less than height H9 to facilitate insertion of leading end portion 146 into the spinal disc space. Upper and lower surfaces 142a, 142b further taper along proximal end 148 to form angle α with the central axis of the insertion instrument.

Figure 19A:
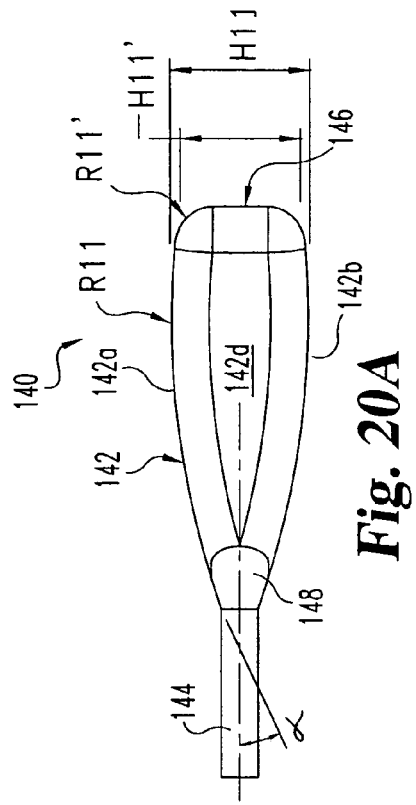
FIGS. 19A and 19B are a plan view and side view, respectively, of a distal portion of another embodiment trial instrument.
Figure 19B:
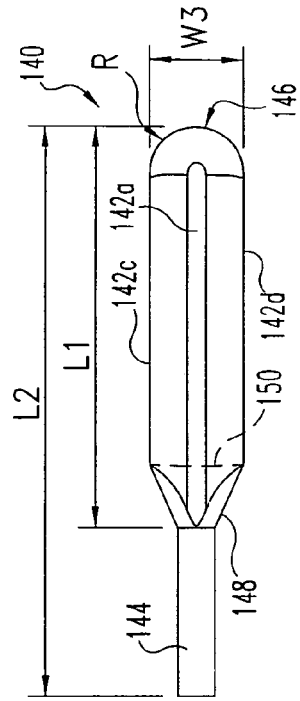

In FIGS. 19A and 19B, distal portion 140 is provided with a body 142 having upper and lower surfaces 142a, 142b curved along radius R10. The upper and lower transition surfaces of leading end portion 146 are curved along radius R10'. Trial body 142 has an overall maximum height H10 between upper and lower surfaces 142a, 142b. Upper and lower surfaces 142a, 142b are curved to provide a height H10' at leading end portion 146. Height H10' is less than height H10 to facilitate insertion of leading end portion 146 into the spinal disc space. Upper and lower surfaces 142a, 142b further taper along proximal end 148 to form angle α with the central axis of the insertion instrument.

Figure 20A:
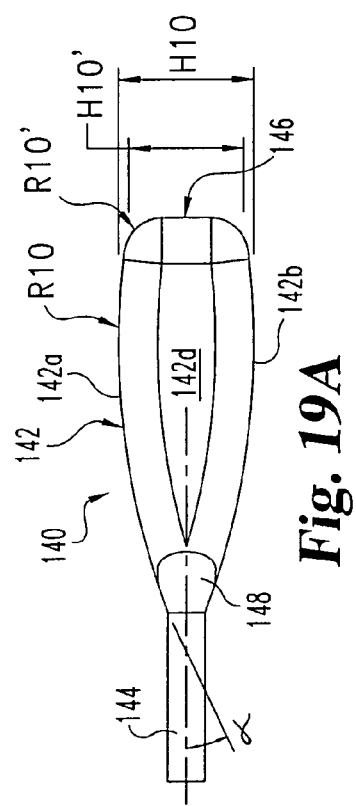
FIGS. 20A and 20B are a plan view and side view, respectively, of a distal portion of another embodiment trial instrument.
Figure 20B:
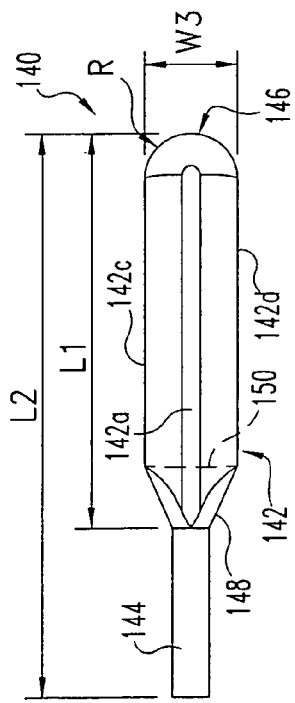

In FIGS. 20A and 20B, distal portion 140 is provided with a body 142 having upper and lower surfaces 142a, 142b curved along radius R11. The upper and lower transition surfaces of leading end portion 146 are curved along radius R11'. Trial body 142 has an overall maximum height H11 between upper and lower surfaces 142a, 142b. Upper and lower surfaces 142a, 142b are curved to provide a height H11' at leading end portion 146. Height H11' is less than height H11 to facilitate insertion of leading end portion 146 into the spinal disc space. Upper and lower surfaces 142a, 142b further taper along proximal end 148 to form angle α with the central axis of the insertion instrument.

It is contemplated that a set of self-distracting implants could be provided by modifying each of the distal portions 140 of FIGS. 11A-20B so that between its distal and proximal ends the implant has a length that fits within a spinal disc space. For example, shaft coupling portion 144 could be removed, or trial body 142 could be truncated at a proximal end wall 150. The proximal end of the implant could includes a threaded hole in the proximal end wall, notches in the lateral walls, or other suitable configuration for releasable engagement with an insertion instrument.

In one specific embodiment of a trial instrument set employing the distal portions of FIGS. 11A-20B, each of the bodies 142 can be provided with a width W3 of about 10 millimeters and a length L1 of about 42 millimeters. Each of the distal portions 140 can be provided with an overall length L2 of about 60 millimeters. Leading end portion 146 can be provided with a radius R of 5 millimeters between lateral surfaces 142c, 142d, and angle α can be about 25 degrees.

In the specific embodiment, height H2 of the FIG. 11A embodiment is 6 millimeters. Each of the heights H3 through H11 can increase in one millimeter increments from height H2 to height H11. Thus, height H11 is 15 millimeters. Furthermore, the reduced height at each of the leading end portions, such as height H2' can be 4 millimeters, or 2 millimeters less than height H2. Similarly, each of the heights H3' through H11' can be 2 millimeters less than the corresponding heights H3 through H11. The radii R2' through R5' transitioning between the nose portion 146a and upper and lower surfaces 142a, 142b can each be 2 millimeters. Radii R6' and R7' can each be 3 millimeters, and radii R8' through R1' can each be 4 millimeters.

The specific embodiment further contemplates that upper and lower surface 142a, 142b have a different curvature for each of the bodies 142 to conform to an adjacent vertebral endplate associated with the particular distraction height provided by the particular body 142. For example, radius R2 can about 221 millimeters, radius R3 can be about 179 millimeters, radius R4 can be about 152 millimeters, radius R5 can be about 133 millimeters, radius R6 can be about 119 millimeters, radius R7 can be about 108 millimeters, radius R8 can be about 100 millimeters, radius R9 can be about 92 millimeters, radius R10 can be about 86 millimeters, and radius R11 can be about 81 millimeters.

While specific dimensional and geometrical features have been provided for one particular embodiment of a set of distal portions 140, it should be understood however, that such dimensional and geometrical attributes are provided for a specific embodiment, and other embodiments contemplate other dimensions than those provided herein.

Figure 21A:
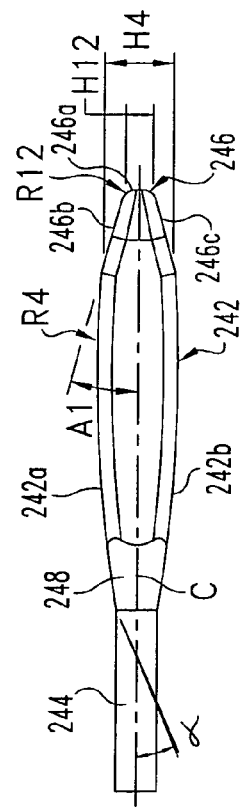
FIGS. 21A and 21B are a plan view and side view, respectively, of a distal portion of another embodiment trial instrument.
Figure 21B:
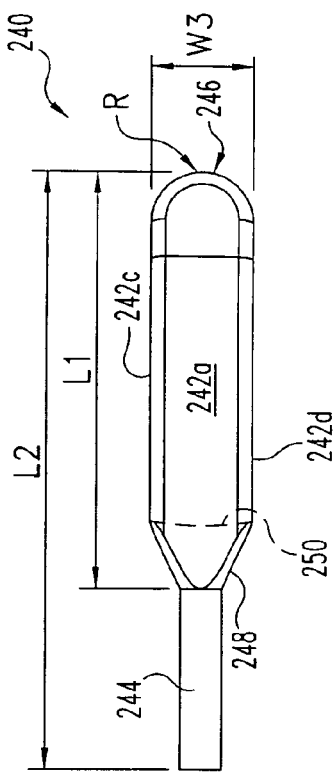

Referring now to FIGS. 21A-21B, there is shown an embodiment of a distal portion 240 of a trial instrument attachable to an insertion instrument. Other embodiment distal portions 240 for trial instruments are shown FIGS. 22A-29B that are similar to the distal portion of FIG. 21A but with differing geometric properties for determining a desired disc space height. However, as discussed further below, the distal portions of FIGS. 22A-29B have geometrical properties which differ from the distal portion 240, providing a set of distal portions 240 which can be sequentially inserted and withdrawn from a collapsed spinal disc space to determine an appropriate implant for insertion therein. In addition, it is contemplated that implants could be provided having the same size and shape of each of the trial bodies of the distal portions 240 shown in FIGS. 21A-29B.

Distal portion 240 includes a trial body 242 and a shaft coupling portion 244 extending proximally therefrom. Shaft coupling portion 244 can be coupled to an insertion instrument. Other embodiments contemplate that trial body 242 can be integral with the insertion instrument. Contemplated coupling arrangements between trial body 242 and the insertion instrument include clamping connections, frictional connections, set screw connections, threaded connections, bayonet connections, and ball-detent connections, for example. Trial body 242 includes an upper surface 242a and a lower surface 242b for contacting the endplate of the adjacent vertebra. Trial body 242 also includes lateral surfaces 242c and 242d. Rounded or tapered lateral transition surfaces extend between upper and lower surfaces 242a, 242b and the respective lateral surfaces 242c, 242d. Trial body 242 further includes a leading end portion 246 and a proximal end 248. Proximal end 248 can tapered to facilitate withdrawal of trial body 242 from the disc space. Leading end portion 246 includes a flat or slightly rounded nose portion 246a and upper and lower transition surfaces 246b, 246c extending therefrom. Upper and lower transition surfaces 246b, 246c provide a gradually increasing distraction height extending from nose portion 246a to facilitate distraction of the adjacent vertebrae.

Distal portion 240 includes an overall length L1, and trial body 242 includes a length L2. Upper and lower surfaces 242a, 242b can be curved along a radius R3 to generally mate with the vertebral endplate geometry. The upper and lower transition surfaces 246b, 246c of leading end portion 246 can be tapered along angle A1 relative to a central axis extending longitudinally through body 242. Trial body 242 includes an overall maximum height H3 between upper and lower surfaces 242a, 242b. Upper and lower surfaces 242a, 242b are tapered from height H3 to height H12 at nose portion 246a. A radius R12 can provide a smooth transition between transition surfaces 246b, 246c and nose portion 246a. Height H12 is less than height H3 to facilitate insertion of leading end portion 246 into the spinal disc space. Trial body 242 can be provided with an overall width W3 between lateral surfaces 242c and 242d.

Figure 22A:
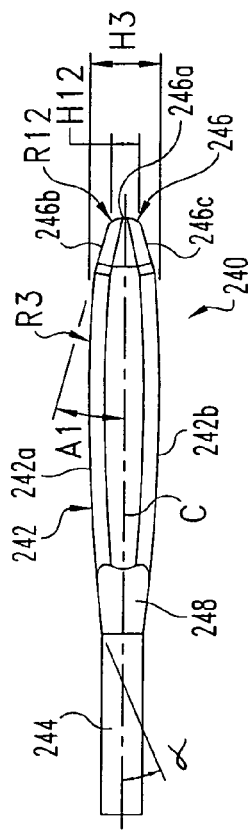
FIGS. 22A and 22B are a plan view and side view, respectively, of a distal portion of another embodiment trial instrument.
Figure 22B:
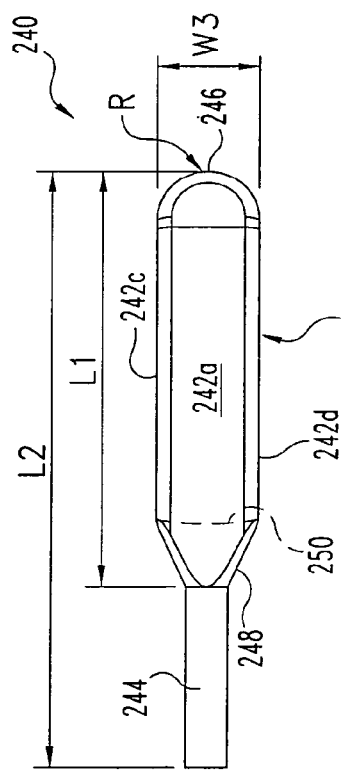

In FIGS. 22A and 22B, distal portion 240 is provided with a body 242 having upper and lower surfaces 242a, 242b curved along radius R4. The upper and lower transition surfaces 246b, 246c of leading end portion 246 can be tapered along angle A1 relative to central axis C extending longitudinally through body 242. Trial body 242 includes an overall maximum height H4 between upper and lower surfaces 242a, 242b. Upper and lower surfaces 242a, 242b are tapered from height H4 to height H12 at nose portion 246a. Radius R12 can provide a smooth transition between transition surfaces 246b, 246c and nose portion 246a. Height H12 is less than height H4 to facilitate insertion of leading end portion 246 into the spinal disc space.

Figure 23A:
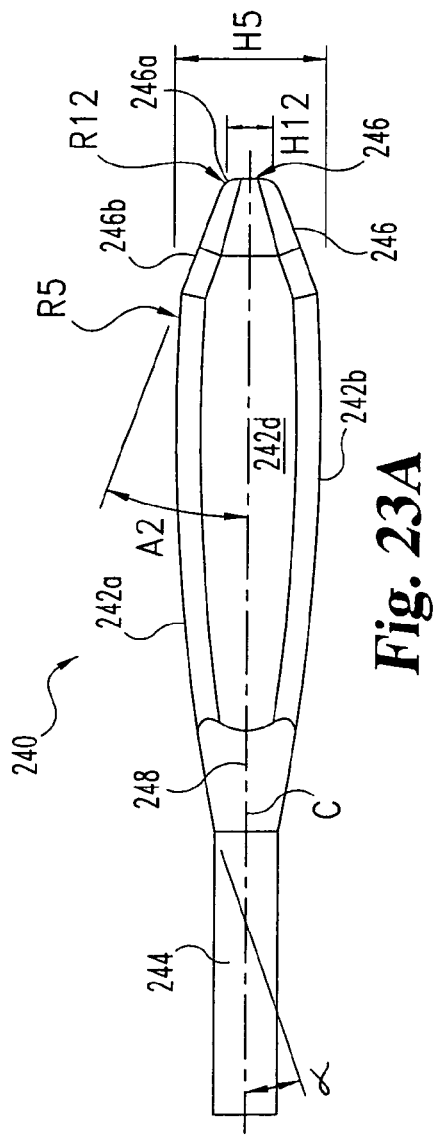
FIGS. 23A and 23B are a plan view and side view, respectively, of a distal portion of another embodiment trial instrument.
Figure 23B:
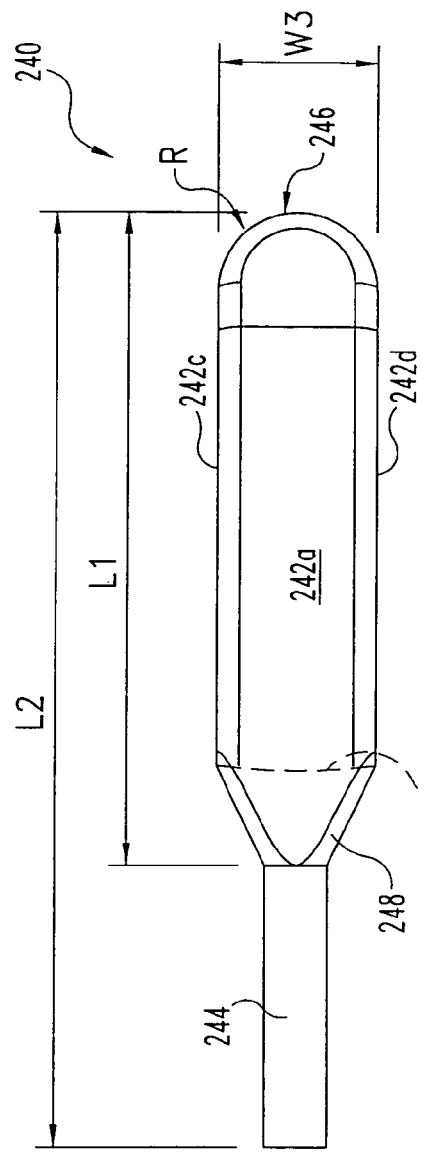

In FIGS. 23A and 23B, distal portion 240 is provided with a body 242 having upper and lower surfaces 242a, 242b curved along radius R5. The upper and lower transition surfaces 246b, 246c of leading end portion 246 can be tapered along angle A2 relative to central axis C extending longitudinally through body 242. Trial body 242 includes an overall maximum height H5 between upper and lower surfaces 242a, 242b. Upper and lower surfaces 242a, 242b are tapered from height H5 to height H12 at nose portion 246a. Radius R12 can provide a smooth transition between transition surfaces 246b, 246c and nose portion 246a. Height H12 is less than height H5 to facilitate insertion of leading end portion 246 into the spinal disc space.

Figure 24A:
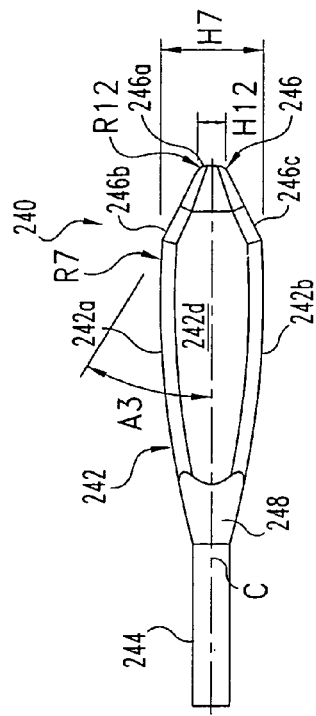
FIGS. 24A and 24B are a plan view and side view, respectively, of a distal portion of another embodiment trial instrument.
Figure 24B:
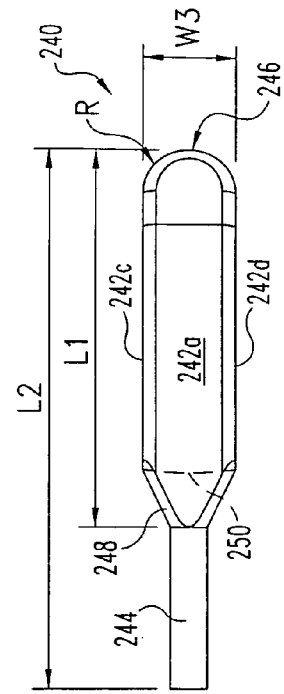

In FIGS. 24A and 24B, distal portion 240 is provided with a body 242 having upper and lower surfaces 242a, 242b curved along radius R6. The upper and lower transition surfaces 246b, 246c of leading end portion 246 can be tapered along angle A2 relative to central axis C extending longitudinally through body 242. Trial body 242 includes an overall maximum height H6 between upper and lower surfaces 242a, 242b. Upper and lower surfaces 242a, 242b are tapered from height H6 to height H12 at nose portion 246a. Radius R12 can provide a smooth transition between transition surfaces 246b, 246c and nose portion 246a. Height H12 is less than height H6 to facilitate insertion of leading end portion 246 into the spinal disc space.

Figure 25A:
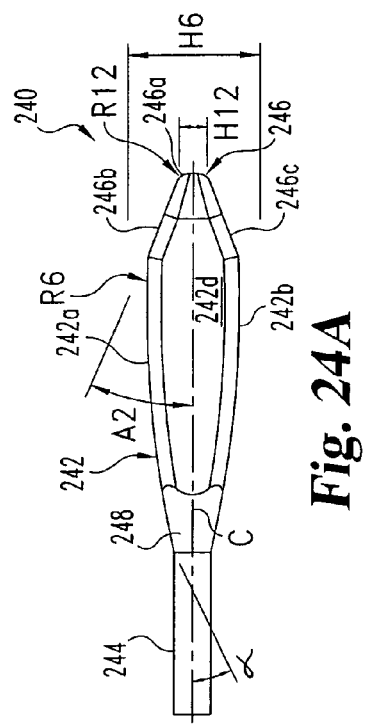
FIGS. 25A and 25B are a plan view and side view, respectively, of a distal portion of another embodiment trial instrument.
Figure 25B:
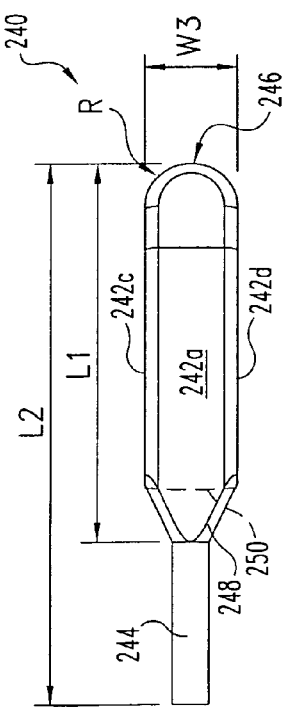

In FIGS. 25A and 25B, distal portion 240 is provided with a body 242 having upper and lower surfaces 242a, 242b curved along radius R7. The upper and lower transition surfaces 246b, 246c of leading end portion 246 can be tapered along angle A3 relative to central axis C extending longitudinally through body 242. Trial body 242 includes an overall maximum height H7 between upper and lower surfaces 242a, 242b. Upper and lower surfaces 242a, 242b are tapered from height H7 to height H12 at nose portion 246a. Radius R12 can provide a smooth transition between transition surfaces 246b, 246c and nose portion 246a. Height H12 is less than height H7 to facilitate insertion of leading end portion 246 into the spinal disc space.

Figure 26A:
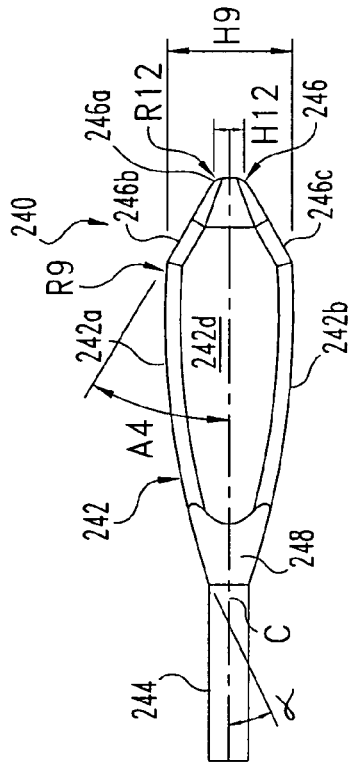
FIGS. 26A and 26B are a plan view and side view, respectively, of a distal portion of another embodiment trial instrument.
Figure 26B:
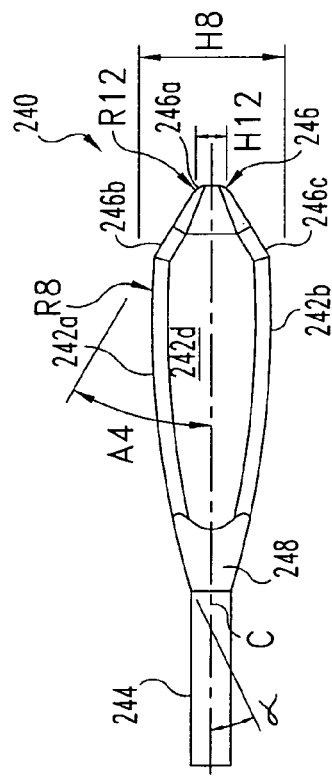

In FIGS. 26A and 26B, distal portion 240 is provided with a body 242 having upper and lower surfaces 242a, 242b curved along radius R8. The upper and lower transition surfaces 246b, 246c of leading end portion 246 can be tapered along angle A4 relative to central axis C extending longitudinally through body 242. Trial body 242 includes an overall maximum height H8 between upper and lower surfaces 242a, 242b. Upper and lower surfaces 242a, 242b are tapered from height H8 to height H12 at nose portion 246a. Radius R12 can provide a smooth transition between transition surfaces 246b, 246c and nose portion 246a. Height H12 is less than height H8 to facilitate insertion of leading end portion 246 into the spinal disc space. Upper and lower surfaces 242a, 242b further taper along proximal end 248 to form angle α with the central axis of the insertion instrument to provide a smooth transition between coupling portion 244 and body 242 to prevent body 242 from hanging up or catching on the vertebral endplates as it is withdrawn.

Figure 27A:
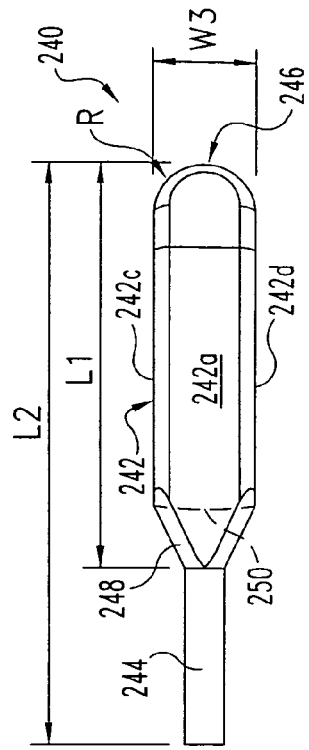
FIGS. 27A and 27B are a plan view and side view, respectively, of a distal portion of another embodiment trial instrument.
Figure 27B:
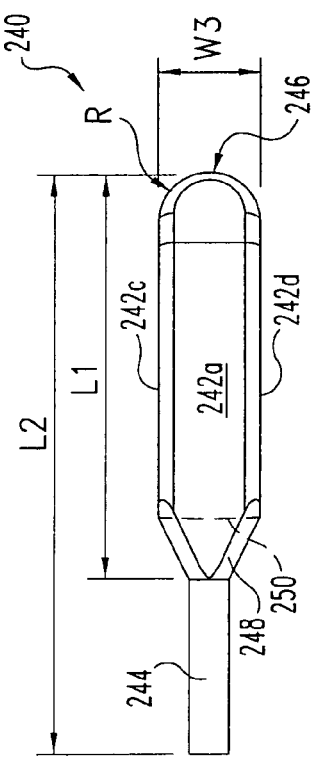

In FIGS. 27A and 27B, distal portion 240 is provided with a body 242 having upper and lower surfaces 242a, 242b curved along radius R9. The upper and lower transition surfaces 246b, 246c of leading end portion 246 can be tapered along angle A4 relative to central axis C extending longitudinally through body 242. Trial body 242 includes an overall maximum height H9 between upper and lower surfaces 242a, 242b. Upper and lower surfaces 242a, 242b are tapered from height H9 to height H12 at nose portion 246a. Radius R12 can provide a smooth transition between transition surfaces 246b, 246c and nose portion 246a. Height H12 is less than height H9 to facilitate insertion of leading end portion 246 into the spinal disc space. Upper and lower surfaces 242a, 242b further taper along proximal end 248 to form angle α with the central axis of the insertion instrument to provide a smooth transition between coupling portion 244 and body 242 to prevent body 242 from hanging up or catching on the vertebral endplates as it is withdrawn.

Figure 28A:
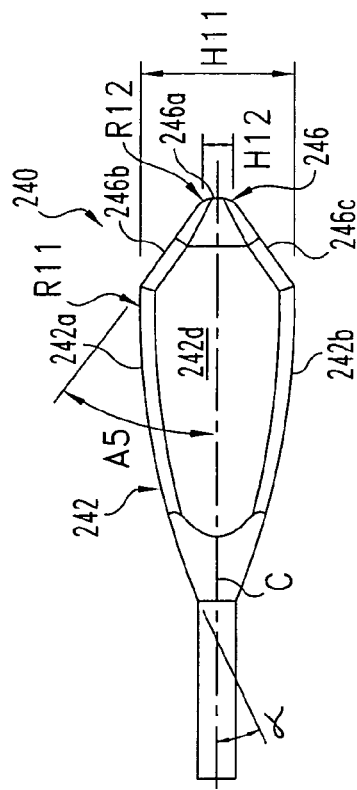
FIGS. 28A and 28B are a plan view and side view, respectively, of a distal portion of another embodiment trial instrument.
Figure 28B:
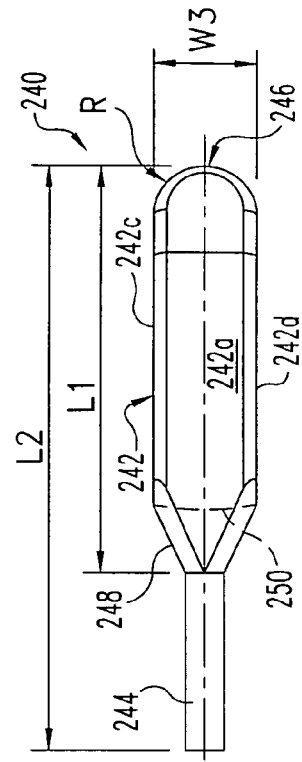

In FIGS. 28A and 28B, distal portion 240 is provided with a body 242 having upper and lower surfaces 242a, 242b curved along radius R10. The upper and lower transition surfaces 246b, 246c of leading end portion 246 can be tapered along angle A4 relative to central axis C extending longitudinally through body 242. Trial body 242 includes an overall maximum height H10 between upper and lower surfaces 242a, 242b. Upper and lower surfaces 242a, 242b are tapered from height H10 to height H12 at nose portion 246a. Radius R12 can provide a smooth transition between transition surfaces 246b, 246c and nose portion 246a. Height H12 is less than height H10 to facilitate insertion of leading end portion 246 into the spinal disc space. Upper and lower surfaces 242a, 242b further taper along proximal end 248 to form angle α with the central axis of the insertion instrument.

Figure 29A:
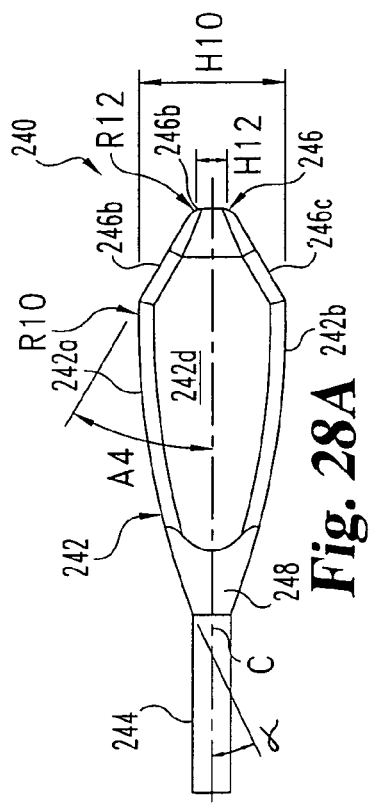
FIGS. 29A and 29B are a plan view and side view, respectively, of a distal portion of another embodiment trial instrument.
Figure 29B:
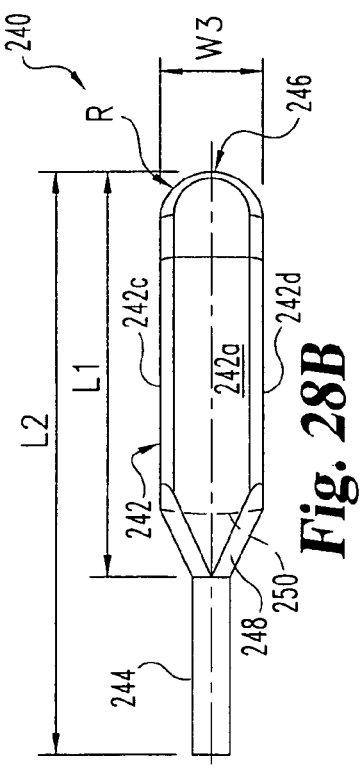

In FIGS. 29A and 29B, distal portion 240 is provided with a body 242 having upper and lower surfaces 242a, 242b curved along radius R11. The upper and lower transition surfaces 246b, 246c of leading end portion 246 can be tapered along angle A5 relative to central axis C extending longitudinally through body 242. Trial body 242 includes an overall maximum height H11 between upper and lower surfaces 242a, 242b. Upper and lower surfaces 242a, 242b are tapered from height H11 to height H12 at nose portion 246a. Radius R12 can provide a smooth transition between transition surfaces 246b, 246c and nose portion 246a. Height H12 is less than height H11 to facilitate insertion of leading end portion 246 into the spinal disc space. Upper and lower surfaces 242a, 242b further taper along proximal end 248 to form angle α with the central axis of the insertion instrument.

It is contemplated that a set of self-distracting implants could be provided by modifying each of the distal portions 240 of FIGS. 21A-29B so that between its distal and proximal ends the implant has a length that fits within a spinal disc space. For example, shaft coupling portion 244 could be removed, or trial body 242 could be truncated at a proximal end wall 250. The proximal end of the implant could includes a threaded hole in the proximal end wall, notches in the lateral walls, or configuration for releasable engagement with an insertion instrument.

In one specific embodiment of a trial instrument set employing the distal portions of FIGS. 21A-29B, each of the bodies 242 can be provided with a width W3 of about 10 millimeters and a length L1 of about 42 millimeters. Each of the distal portions 240 can be provided with an overall length L2 of about 60 millimeters. Leading end portion 246 can be provided with a radius R of 5 millimeters between lateral surfaces 242c, 242d.

In the specific embodiment, height H3 of the FIG. 21A embodiment is 7 millimeters. Each of the heights H4 through H11 increase in one millimeter increments from height H3 to height H11. Thus, height H11 is 15 millimeters. Height H12 at nose portion 246a is 3 millimeters for each of the bodies 242. The radii R12 transitioning between nose portion 246a and upper and lower transition surfaces 246b, 246c can be about 1.5 millimeters.

Transition surfaces 246b, 246c extend between radius R12 and the adjacent upper and lower surface 242a, 242b. The angular orientation of transition surfaces 246b, 246c relative to the central axis of the body 242 can range from angle A1 to angle A5 for various ones of the embodiments shown. In one specific embodiment trial instrument set, angle A1 is about 15 degrees, angle A2 is about 20 degrees, angle A3 is about 25 degrees, angle A4 is about 30 degrees, and angle A5 is about 35 degrees. The specific embodiment further contemplates that upper and lower surface 242a, 242b can be provided with a different curvature for each of the bodies 242. For example, radius R3 can be about 179 millimeters, radius R4 can be about 152 millimeters, radius R5 can be about 133 millimeters, radius R6 can be about 119 millimeters, radius R7 can be about 108 millimeters, radius R8 can be about 100 millimeters, radius R9 can be about 92 millimeters, radius RIO can be about 86 millimeters, and radius R11 can be about 81 millimeters.

While specific dimensional and geometrical features have been provided for one particular embodiment of a set of distal portions 240, it should be understood however, that such dimensional and geometrical attributes are provided for a specific embodiment, and other embodiments contemplate other dimensions than those provided herein.

The present invention contemplates various procedures and instrument sets. For example, the surgeon can determine whether a trial body or implant provides a desired disc space height by tactile feedback of the inserted trial body or implant, and also by visual inspection. The inserted trial body or implant body should sufficiently stretch the remaining annulus tissue to provide firm engagement between the upper and lower surfaces of the trial or implant body and the adjacent vertebral endplates. Sufficient surface area contact should be present to prevent or minimize post-operative movement of the adjacent vertebrae relative to the implant. By providing the trial bodies and implant bodies with correspondingly sized and shaped leading end portions, and by inserting the trial bodies and implant bodies in a non-distracted disc space, the inserted trial or implant body provides immediate feedback to the surgeon of the desirability of the fit. If distraction were maintained by, for example, a second distractor, feedback to the surgeon of the post-operative fit of the implant would not be reliable or available, if at all, until distraction were removed. As such, the trial bodies and implants can be employed without utilization of external distraction or distraction maintained in another disc space location during trial body and implant insertion. However, secondary distraction can be used to at least partially maintain disc space distraction upon withdrawal of the implants and trial bodies can be employed. For example, pedicle screws and a rod can be employed on the contralateral side to at least partially maintain distraction obtained with a particular implant or trial body.

Further, the trial bodies provide an indication of the fit of the implant into the disc space location. Since the implant includes a leading end portion and height that corresponds to that of the trial body, there is an immediate confirmation to the surgeon that the corresponding implant will fit into the space occupied by the trial body. If distraction were maintained at another location in the disc space or externally, there is no indication that the implant will fit properly until the implant is inserted and distraction removed. As a result, the implant may wedge too tightly in the disc space when distraction is removed, making subsequent removal of the implant difficult if an appropriate fit is not obtained. Alternatively, the implant may be too loose when the distraction is removed due to over distraction of the disc space.

The implants can be impacted or pushed into the disc space. As a result, disruption to the annulus tissue and tissue approaching the collapsed disc space is minimized since the lateral and vertical footprint of the implant in the disc space can be the same as the lateral and vertical footprint occupied in the implant's approach to the disc space. Also, by providing the implant with the same footprint as the trial body laterally and vertically, and by performing distraction and implant insertion through the same portal or pathway, no additional tissue dissection and/or retraction is required to accommodate distraction of the disc space during implant insertion.

The trial bodies and implants can be inserted into the disc space with minimal disc space preparation. According to one method, the collapsed disc space is accessed, and an opening is formed in the annulus having a width corresponding to the width of the trial bodies and/or implants. Disc material is removed through the annulus opening, and, if desired by the surgeon, manual roughening of the endplates is performed with a scraper or other suitable endplate roughening instrument. The trial bodies and/or implant bodies are then sequentially inserted and, if necessary, withdrawn through the annulus opening and into the disc space. Since the implants are self-distracting, it is not necessary to chisel, drill or otherwise form the vertebral endplates to receive the implant, although such steps are not precluded. Consequently, fewer steps in the surgical procedure are necessary since requirements for bilateral distraction, external distraction, chiseling, drilling and reaming are eliminated. In addition, the lack of other instruments or devices in the disc space facilitates visualization of the disc space preparation, trial body insertion, and/or implant insertion. Elimination of cutting instruments in the disc space also theoretically improves the safety of the procedure.

Minimally invasive techniques employing the trial instruments and implants are contemplated. In any particular patient, the implants can be inserted via any one or combination of posterior, postero-lateral, antero-lateral, transforaminal, far lateral and/or anterior approaches. Implant insertion can occur through a single pathway to a collapsed spinal disc space, or through multiple pathways to the collapsed disc space, or through multiple pathways to multiple levels of collapsed discs of the spinal column. Since the implant, and trial instruments if employed, are inserted into the same disc space location from the same approach, the entire procedure for inserting an implant can be completed through one pathway. If a multiple pathway procedure is to be employed, the surgeon can complete implant insertion through one pathway before creating and moving to work in a second pathway.

Since distraction and implant insertion occur along the same pathway to the collapsed disc space, the implants and trial instruments are suited for use in minimally invasive procedures which employ a retractor sleeve to provide a pathway to the collapsed disc space. Such retractor sleeves can employ any one or combination of an endoscopic viewing element in the working channel, a microscopic viewing system over the proximal end of the retractor sleeve, fluoroscopic viewing, loupes, naked eye and/or image guidance.

The trial bodies of the trial instruments and the implant bodies can be made from any biocompatible material, including synthetic or natural autograft, allograft or xenograft tissues, and can be resorbable or non-resorbable in nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are non-reinforced polymers, carbon-reinforced polymer composites, PEEK and PEEK composites, shape-memory alloys, titanium, titanium alloys, cobalt chrome alloys, stainless steel, ceramics and combinations thereof and others as well. If the trial body or implant is made from radiolucent material, radiographic markers can be located on the trial body or implant to provide the ability to monitor and determine radiographically or fluoroscopically the location of the body in the spinal disc space. The material comprising the trial bodies can be solid, porous, spongy, perforated, drilled, and/or open.

There is contemplated an implant for insertion into a spinal disc space between adjacent vertebrae. The implant can be impacted or pushed into the disc space. The implant can be provided with a distal end or leading insertion end that is sized for insertion into the collapsed disc space. As the implant is inserted, the implant can restore the collapsed disc space to a desired disc space height. The desired disc space height corresponds to the height of the implant proximal the distal end. Once inserted, the implant can maintain the disc space at the desired disc space height.

There is further contemplated an implant that, when inserted, restores and maintains a desired disc space height of a collapsed disc space between an upper vertebra and a lower vertebra. The implant includes a body with a distal end, a proximal end, an upper surface orientable toward an endplate of the upper vertebra and a lower surface orientable toward an endplate of the lower vertebra. The body of the implant has a first height between the upper and lower surfaces corresponding to the desired disc space height. The body of the implant also has a second height at its distal end that is less than a height of the collapsed disc space.

It is contemplated that the implants can be provided with bi-convex curvature of the upper and lower surfaces, allowing the implants to center in the endplates of the disc space. It is further contemplated that the upper and lower surfaces of the implant can be planar or include compound geometry. The upper and lower surfaces of the implant can also be configured to establish lordotic or kyphotic angulation between the adjacent vertebral bodies.

Also contemplated is a set of implants having two or more implants of increasing height. The height of each implant corresponds to a restored disc space height. The leading insertion end of each implant is sized for insertion into a collapsed disc space. As each implant is inserted, the implant restores the collapsed disc space to the restored disc space height provided by the inserted implant. If the restored disc space height does not correspond to the desired disc space height, the inserted implant is withdrawn and a larger height implant is inserted. Sequential insertion and withdrawal of increasing height implants is continued until the restored disc space height provided by an implant of the set of implants corresponds to the desired disc space height. The implant providing the desired disc space height is positioned in the disc space to restore and post-operatively maintain the desired disc space height.

There is further contemplated an instrument set having two or more self-distracting trial instruments and at least one implant. The two or more trial instruments each have a body with a leading insertion end sized for insertion into a collapsed disc space. The leading insertion ends of each trial body are substantially the same in size and shape. Each trial body has a height proximal the leading insertion end that restores the collapsed disc space height to a height different than that of the other trial bodies. The at least one implant has a leading insertion end that is substantially the same in size and shape as the leading insertion end of at least one of the trial bodies of the trial instruments. The implant has a height proximal its leading insertion end that corresponds to the desired restored disc space height provided by the at least one trial body.

Also contemplated is a kit including a set of trial instruments, each having a trial body at a distal end thereof. The trial bodies have a self-distracting leading end portion insertable in a collapsed spinal disc space. The kit further includes a set of implants positionable in the collapsed spinal disc space. Each implant has a body sized and shaped to correspond in size and shape to a respective trial body of the trial instruments. The fit of each implant body in the spinal disc space is indicated to the surgeon by the fit of the corresponding trial body of the trial instruments. When a trial body provides a desired fit, the trial body is removed and the implant corresponding to the trial body is inserted into the collapsed disc space in the location previously occupied by the withdrawn trial body.

It is contemplated that an insertion instrument can be engaged to lateral walls of an intervertebral implant. The insertion instrument includes a distal coupling portion positionable in notches formed in corresponding ones of the lateral walls of the implant. The coupling portion has a first position engaging the implant in the notches and a second position disengaged from the implant in the notches. The width of the coupling portion in each of its first and second positions is less than the width of the implant between the lateral walls of the implant.

Methods for inserting an intervertebral implant into a collapsed spinal disc space are also contemplated. A number of implants are sequentially inserted into the collapsed disc space to restore the disc space. If a particular implant does not restore the disc space to a desired disc space height, the implant is withdrawn from the disc space. When an inserted implant is withdrawn, the disc space is non-distracted and allowed to collapse. The implant providing the desired disc space height remains in the disc space to post-operatively maintain the desired disc space height.

A method is contemplated for inserting an intervertebral implant that includes accessing a collapsed spinal disc space from an uni-portal approach. A first implant is inserted through the portal into the disc space to restore the disc space height. If the restored disc space height does not correspond to a desired disc space height, the inserted implant is removed from the disc space and portal, and the disc space is allowed to collapse. A second implant of different height is inserted into the undistracted, collapsed disc space to provide another restored disc space height. When an inserted implant provides a restored disc space height that corresponds to a desired disc space height, the inserted implant remains in the disc space to post-operatively maintain the desired disc space height.

Also contemplated is a method for inserting an intervertebral implant is provided that includes accessing a collapsed spinal disc space. A number of trial bodies are provided with leading end portions sized for insertion into a non-distracted disc space. The trial bodies are sequentially inserted into and removed from the disc space. The trial body providing the desired disc space height is used to select an implant having a height and a self-distracting leading end portion corresponding to the height and leading end portion of the last inserted trial body. The implant is then inserted into the non-distracted disc space to restore the disc space and post-operatively maintain the desired disc space height.

While the invention has been illustrated and described in detail in the drawings and foregoing description, the same is to be considered as illustrative and not restrictive in character, and that all changes and modifications that come within the spirit of the invention are desired to be protected.

What is claimed is:

1. A kit, comprising:
   a set of trial instruments, at least two of said trial instruments of said set having a trial body at a distal end thereof, each of said trial bodies having a leading end portion adapted for insertion in a collapsed spinal disc space and being insertable into the collapsed spinal disc space to provide a restored disc space height; and
   a set of implants positionable in the spinal disc space, each of said implants including a body sized and shaped to correspond in size and shape to a respective one of said trial bodies of said trial instruments, each of said bodies having a leading end portion adapted for insertion in a collapsed spinal disc space and opposite vertebral endplate contacting surfaces convexly curved from said leading end portion to a proximal end wall of said body, wherein a desired one of said set of implants is selected for insertion into the spinal disc space upon an indication to the surgeon of a desired fit in the spinal disc space provided by the respective trial body.

2. The kit of claim 1, wherein each leading end portion of said bodies of said implants includes a nose portion having the same height for each body in said set of implants.

3. The kit of claim 2, wherein each leading end portion of said trial bodies includes a nose portion having the same height for each trial body in said set of trial instruments.

4. The kit of claim 3, wherein said height of said nose portions is about 3 to 4 millimeters.

5. The kit of claim 3, wherein said nose portion of each of said bodies of said implants and each of said trial bodies is rounded between an upper surface and a lower surface of said respective body of said implant and said trial body.

6. The kit of claim 5, wherein each of said implant bodies and said trial bodies includes an upper transition surface and a lower transition surface along said leading end portion thereof tapering from said respective upper surface and said lower surface to said rounded nose portion thereof.

7. The kit of claim 6, wherein said upper and lower transition surfaces are planar.

8. The kit of claim 6, wherein said upper and lower transition surfaces are convexly curved.

9. The kit of claim 5, wherein said nose portion of each of said trial bodies and each of said bodies of said implants is convexly curved in the direction between opposite lateral sidewalls of said respective trial body and said respective body of said implants.

10. The kit of claim 1, where each of said bodies of said implants includes an upper surface orientable toward an endplate of an upper vertebra and a lower surface orientable toward an endplate of a lower vertebra, said body including a first height between said upper and lower surfaces corresponding to the restored disc space height.

11. The kit of claim 1, wherein each of said trial bodies includes an upper surface and an opposite lower surface and said leading end portion includes a convexly curved nose extending between said upper and lower surfaces, wherein said upper and lower surfaces are also convexly curved along said respective trial body.

12. The kit of claim 11, wherein each of said bodies of said implants includes an upper surface and an opposite lower surface and said leading end portion includes a convexly curved nose extending between said upper and lower surfaces.

13. The kit of claim 11, wherein said nose of each of said trial bodies is convexly rounded between opposite lateral surfaces of said trial body, said lateral surfaces extending parallel to one another and between said upper and lower surfaces.

14. The kit of claim 1, wherein each of said bodies of said implants includes an upper surface and an opposite lower surface and said leading end portion includes a convexly curved nose extending between said upper and lower surfaces.

15. The kit of claim 1, wherein each of said bodies of said implants is releasably engageable to an insertion instrument and structured to post-operatively maintain the collapsed disc space at the restored disc space height.

16. A kit, comprising:
    a set of trial instruments, at least two of said trial instruments of said set including an elongated trial body at a distal end thereof, each of said trial bodies including a leading end portion adapted for insertion in a spinal disc space, said trial bodies further each including convexly curved upper and lower surfaces defining a height to provide a restored disc space height when inserted in the spinal disc space, wherein each of said trial bodies further includes a leading end nose convexly rounded between said upper and lower surfaces; and
    a set of implants positionable in the spinal disc space, each of said implants including an elongated body sized and shaped to correspond in size and shape to a respective one of said trial bodies of said trial instruments, each of said implant bodies including upper and lower surfaces and a leading end portion defining a convexly rounded nose extending between said upper and lower surfaces, said upper and lower surfaces being convexly curved from said leading end portion to a proximal wall of said implant body and defining a height corresponding to said height of a respective one of said trial bodies, wherein one of said implants is selected for insertion into the spinal disc space upon an indication to the surgeon of a desired fit in the spinal disc space provided by said respective trial body.

17. The kit of claim 16, wherein:
    said trial bodies each include opposite parallel lateral surfaces and said nose thereof is convexly rounded between said lateral surfaces; and
    said implant bodies each include opposite parallel lateral surfaces and said nose thereof is convexly rounded in the direction between said lateral surfaces.

18. A kit, comprising:
    a set of trial instruments, at least two of said trial instruments of said set including an elongated trial body at a distal end thereof, each of said trial bodies including a leading end portion adapted for insertion in a spinal disc space, said trial bodies further each including convexly curved upper and lower surfaces defining a height to provide a restored disc space height when inserted in the spinal disc space, wherein each of said trial bodies further includes opposite parallel lateral surfaces extending between said upper and lower surfaces and a leading end nose convexly rounded between said opposite lateral surfaces; and a set of implants positionable in the spinal disc space, each of said implants including an elongated body sized and shaped to correspond in size and shape to a respective one of said trial bodies of said trial instruments, each of said implant bodies including convexly curved upper and lower surfaces defining a height corresponding to said height of a respective one of said trial bodies, said implant bodies further including opposite parallel lateral surfaces extending between said upper and lower surfaces and a leading end portion defining nose convexly rounded in the direction extending between said opposite lateral surfaces, wherein one of said implants is selected for insertion into the spinal disc space upon an indication to the surgeon of a desired fit in the spinal disc space provided by the respective trial body.

19. The kit of claim 18, wherein:

said nose of each of said trial bodies is convexly rounded between said upper and lower surfaces; and said nose of each of said implant bodies is convexly rounded between said upper and lower surfaces.

20. The kit of claim 18, further comprising an elongated shaft extending proximally from each of said trial bodies and an inserter instrument removably engageable to respective ones of said implants.

* * * * *